(12) United States Patent
Hashimoto et al.

(10) Patent No.: US 12,080,386 B2
(45) Date of Patent: Sep. 3, 2024

(54) DIAGNOSIS/TREATMENT ASSISTING APPARATUS AND DIAGNOSIS/TREATMENT ASSISTING SYSTEM

(71) Applicant: CANON MEDICAL SYSTEMS CORPORATION, Otawara (JP)

(72) Inventors: Keisuke Hashimoto, Nasushiobara (JP); Shintaro Niwa, Nasushiobara (JP); Mariko Shibata, Nasushiobara (JP); Michitaka Sugawara, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 503 days.

(21) Appl. No.: 17/026,361

(22) Filed: Sep. 21, 2020

(65) Prior Publication Data
US 2021/0098088 A1   Apr. 1, 2021

(30) Foreign Application Priority Data

Sep. 26, 2019   (JP) ................................ 2019-175982

(51) Int. Cl.
*G16H 10/20*    (2018.01)
*G06F 40/30*    (2020.01)
(Continued)

(52) U.S. Cl.
CPC ............. *G16H 10/20* (2018.01); *G06F 40/30* (2020.01); *G06Q 10/105* (2013.01); *G06Q 50/01* (2013.01);
(Continued)

(58) Field of Classification Search
CPC ........ G16H 10/20; G16H 10/60; G16H 50/20; G16H 50/30; G16H 50/70; G16H 80/00; G06F 40/30; G06Q 10/105; G06Q 50/01
See application file for complete search history.

(56) References Cited

U.S. PATENT DOCUMENTS

| 9,552,354 B1 * | 1/2017 | Seligman ................ G06F 40/51 |
| 2009/0089082 A1 * | 4/2009 | Heckerman ............ G16H 10/20 |
| | | 705/2 |

(Continued)

FOREIGN PATENT DOCUMENTS

| JP | 2005-078259 A | 3/2005 |
| JP | 2011-193989 A | 10/2011 |

(Continued)

OTHER PUBLICATIONS

Japanese Office Action issued Sep. 26, 2023, in Japanese Patent Application No. 2019-175982, 4 pages.

*Primary Examiner* — Chad A Newton
(74) *Attorney, Agent, or Firm* — Oblon, McClelland, Maier & Neustadt, L.L.P.

(57) ABSTRACT

A diagnosis assisting apparatus according to an embodiment includes a processing circuit and a display circuit. The processing circuit is configured to obtain a first question represented by a question from a patient to a medical doctor. The processing circuit is configured to analyze content of the obtained first question. The processing circuit is configured to convert the first question into a second question having equivalent content and using a different expression, on the basis of a result of the analysis. The display circuit is configured to display the second question.

18 Claims, 21 Drawing Sheets

| PRE-CONVERSION QUESTIONS | POST-CONVERSION QUESTIONS |
|---|---|
| I DON'T WANT TO HAVE SURGERY. | ·WHAT WOULD BE THE MEDICAL DISADVANTAGES IF I DON'T HAVE THIS TREATMENT? I DON'T WANT TO SUFFER FROM THE SIDE EFFECTS OF ANTI-CANCER DRUGS. ·HOW MUCH WILL THE TREATMENT COST? I'M WORRIED ABOUT THE EXPENSES. ·COULD YOU PLEASE REFER ME TO A FACILITY THAT OFFERS TREATMENT IN MY NEIGHBORHOOD? |
| I DON'T WANT TO BE UNABLE TO HAVE BABIES. | ·COULD YOU PLEASE RECOMMEND A TREATMENT METHOD THAT ENSURES FERTILITY? ·COULD YOU PLEASE TELL ME ABOUT PREGNANCY AFTER THE TREATMENT, LIKE OOCYTE CRYOPRESERVATION? |
| I DON'T KNOW WHAT TO DO. | ·COULD YOU PLEASE PROVIDE AN EASY-TO-UNDERSTAND EXPLANATION (USING A COMPARISON TABLE) OF THE CHARACTERISTICS AND DIFFERENCES AMONG THE ANTI-CANCER DRUGS (DOSING PERIODS AND SIDE EFFECTS)? ·WHICH TREATMENT METHOD IS CHOSEN BY MANY OF THE PATIENTS? ·IF YOUR RELATIVE WAS A PATIENT, WHICH TREATMENT METHOD WOULD YOU CHOOSE? |
| I DON'T TRUST/LIKE THAT DOCTOR. IS HE [SHE] COMPETENT? | ·HOW MANY SURGERIES A YEAR DO YOU PERFORM? ·YOU ARE A MEDICAL INSTRUCTOR, AREN'T YOU? ·COULD I PLEASE REQUEST A FEMALE DOCTOR BECAUSE I'D BE EMBARRASSED? |
| THIS TREATMENT IS EXPENSIVE, ISN'T IT? | COULD YOU PLEASE PROVIDE AN EASY-TO-UNDERSTAND EXPLANATION OF THE MEDICAL EXPENSES THAT I MAY HAVE IF WE USE THIS NEW DRUG? |
| CHEMOTHERAPY TREATMENT IS STRENUOUS, ISN'T IT? | ·COULD YOU PLEASE CONSIDER TREATMENT METHODS WHILE PRIORITIZING ANTI-CANCER DRUGS THAT HAVE LESS SIDE EFFECTS? ·IF I HAVE STRONG SIDE EFFECTS, CAN I SWITCH TO AN ALTERNATIVE TREATMENT METHOD? ·IF WE CHOOSE HEAVY ION THERAPY OR RADIATION THERAPY, HOW MUCH LESS EFFECTIVE ARE THEY COMPARED TO OTHER TREATMENT METHODS? |
| WHY SHOULD I SUFFER FROM CANCER? | THE PATIENT DOES NOT HAVE MUCH MEDICAL KNOWLEDGE. COULD YOU PLEASE EXPLAIN ABOUT CANCER STATISTICS (ONE IN TWO PEOPLE HAS CANCER) AND TELL THE PATIENT THAT IT IS NOT HIS [HER] FAULT? |

(51) Int. Cl.
    *G06Q 10/105* (2023.01)
    *G06Q 50/00* (2012.01)
    *G16H 10/60* (2018.01)
    *G16H 50/20* (2018.01)
    *G16H 50/30* (2018.01)
    *G16H 50/70* (2018.01)

(52) U.S. Cl.
    CPC ............. *G16H 10/60* (2018.01); *G16H 50/20* (2018.01); *G16H 50/30* (2018.01); *G16H 50/70* (2018.01)

(56) References Cited

U.S. PATENT DOCUMENTS

| | | |
|---|---|---|
| 2011/0227574 A1 | 9/2011 | Akita et al. |
| 2014/0062480 A1 | 3/2014 | Bollenbeck et al. |
| 2015/0216413 A1* | 8/2015 | Soyao .................... H04L 67/12 709/204 |
| 2019/0392813 A1* | 12/2019 | Jiang .................... G10L 13/047 |

FOREIGN PATENT DOCUMENTS

| | | |
|---|---|---|
| JP | 2014-050712 A | 3/2014 |
| JP | 2017-027233 A | 2/2017 |
| JP | 2018-013997 A | 1/2018 |

\* cited by examiner

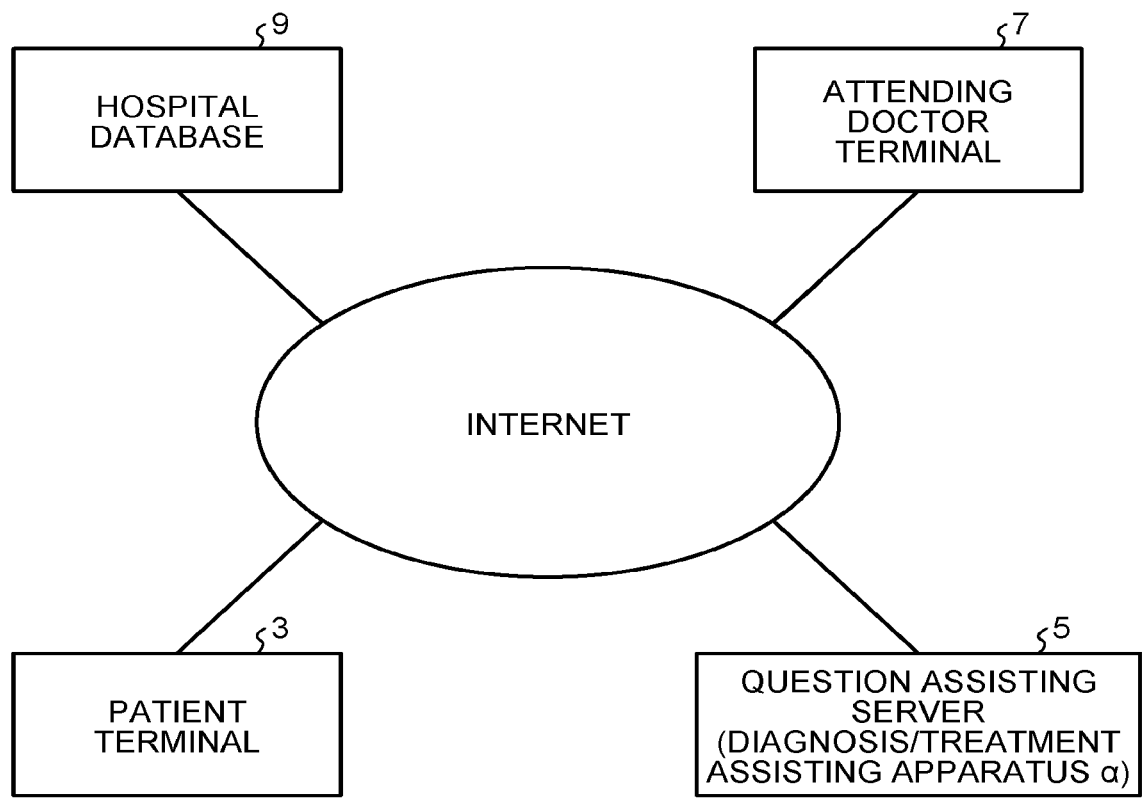

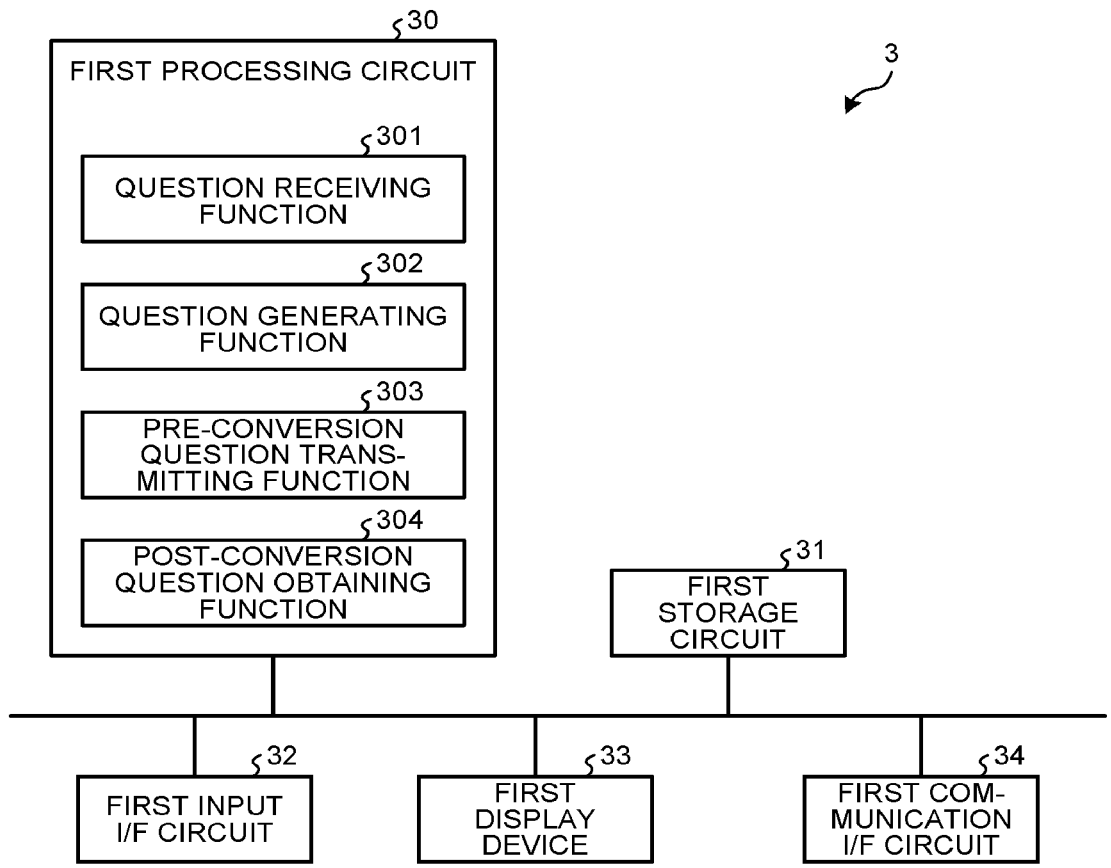

FIG.2

FIRST PROCESSING CIRCUIT (30)
- QUESTION RECEIVING FUNCTION (301)
- QUESTION GENERATING FUNCTION (302)
- PRE-CONVERSION QUESTION TRANSMITTING FUNCTION (303)
- POST-CONVERSION QUESTION OBTAINING FUNCTION (304)

FIRST STORAGE CIRCUIT (31)

FIRST INPUT I/F CIRCUIT (32) | FIRST DISPLAY DEVICE (33) | FIRST COMMUNICATION I/F CIRCUIT (34)

FIG.3

| PRE-CONVERSION QUESTIONS |
| --- |
| THIS DOCTOR SEEMS UNRELIABLE. CAN I TRUST THIS DOCTOR? |
| I DON'T LIKE THIS DOCTOR. I'D LIKE TO REQUEST A DIFFERENT DOCTOR. |
| I'M WORRIED THAT A YOUNGER DOCTOR MAY TAKE OVER ON THAT DAY AND MAKE A MISTAKE. |
| WILL I REALLY BE CURED WITH THIS TREATMENT? |
| I WANT TO BE TREATED WITH THE OTHER TREATMENT METHOD. |
| I DON'T WANT TO GO UNDER THE KNIFE. CAN I DO SOMETHING ELSE? |
| DOES IT HAVE TO BE NOW? CAN I WAIT AND SEE? |
| THIS TREATMENT IS TOO EXPENSIVE. CAN I DISCONTINUE IT? |

| PRE-CONVERSION QUESTIONS |
|---|
| I DON'T WANT TO HAVE SURGERY. |
| I DON'T WANT TO BE UNABLE TO HAVE BABIES. |
| I DON'T KNOW WHAT TO DO. |
| I DON'T TRUST/LIKE THAT DOCTOR. IS HE [SHE] COMPETENT? |
| THIS TREATMENT IS EXPENSIVE, ISN'T IT? |
| CHEMOTHERAPY TREATMENT IS STRENUOUS, ISN'T IT? |
| WHY SHOULD I SUFFER FROM CANCER? |

FIG.6

| PRE-CONVERSION QUESTIONS | POST-CONVERSION QUESTIONS |
|---|---|
| THIS DOCTOR SEEMS UNRELIABLE. CAN I TRUST THIS DOCTOR? | I'D LIKE TO HAVE THE SURGERY WITH AN EXPERIENCED DOCTOR. WOULD IT BE POSSIBLE TO REQUEST THE DOCTOR WHO IS THE HEAD OF THE DEPARTMENT? |
| I DON'T LIKE THIS DOCTOR. I'D LIKE TO REQUEST A DIFFERENT DOCTOR. | I APPRECIATE THAT YOU CAN OPERATE ON ME, DOCTOR, BUT I'D LIKE TO GIVE DR. XX WHO IS YOUNGER AN OPPORTUNITY TO LEARN. WHAT DO YOU THINK? |
| I'M WORRIED THAT A YOUNGER DOCTOR MAY TAKE OVER ON THAT DAY AND MAKE A MISTAKE. | IS THERE ANY CHANCE THAT YOU MAY SWITCH THE DOCTOR SCHEDULED TO PERFORM THE SURGERY ON THAT DAY? I'D LIKE TO MAKE SURE THAT I HAVE THIS DOCTOR. |
| WILL I REALLY BE CURED WITH THIS TREATMENT? | I'D LIKE TO BE ASSURED THAT THIS IS THE BEST TREATMENT METHOD. WOULD YOU PLEASE EXPLAIN WHY THIS METHOD IS BETTER THAN OTHER TREATMENT METHODS? |
| I WANT TO BE TREATED WITH THE OTHER TREATMENT METHOD. | I UNDERSTAND THIS TREATMENT METHOD IS MOST SUITABLE FOR ME, BUT I'D LIKE TO DECIDE MY TREATMENT PLAN AFTER UNDERSTANDING METHOD XX. COULD YOU PLEASE EXPLAIN IT TO ME AS A SECOND OPINION? |
| I DON'T WANT TO GO UNDER THE KNIFE. CAN I DO SOMETHING ELSE? | I'M UNEASY ABOUT HAVING SURGERY. COULD YOU PLEASE PROCEED WITH MAINLY RADIATION THERAPY? |
| DOES IT HAVE TO BE NOW? CAN I WAIT AND SEE? | IF THE TREATMENT IS POSTPONED, WHAT DISADVANTAGES MIGHT I HAVE? |
| THIS TREATMENT IS TOO EXPENSIVE. CAN I DISCONTINUE IT? | THE FINANCIAL BURDEN IS TOO GREAT. WOULD IT BE POSSIBLE TO SELECT ANOTHER TREATMENT METHOD? |

FIG.7

| PRE-CONVERSION QUESTIONS | POST-CONVERSION QUESTIONS |
|---|---|
| I DON'T WANT TO HAVE SURGERY. | ·WHAT WOULD BE THE MEDICAL DISADVANTAGES IF I DON'T HAVE THIS TREATMENT? I DON'T WANT TO SUFFER FROM THE SIDE EFFECTS OF ANTI-CANCER DRUGS.<br>·HOW MUCH WILL THE TREATMENT COST? I'M WORRIED ABOUT THE EXPENSES.<br>·COULD YOU PLEASE REFER ME TO A FACILITY THAT OFFERS TREATMENT IN MY NEIGHBORHOOD? |
| I DON'T WANT TO BE UNABLE TO HAVE BABIES. | ·COULD YOU PLEASE RECOMMEND A TREATMENT METHOD THAT ENSURES FERTILITY?<br>·COULD YOU PLEASE TELL ME ABOUT PREGNANCY AFTER THE TREATMENT, LIKE OOCYTE CRYOPRESERVATION? |
| I DON'T KNOW WHAT TO DO. | ·COULD YOU PLEASE PROVIDE AN EASY-TO-UNDERSTAND EXPLANATION (USING A COMPARISON TABLE) OF THE CHARACTERISTICS AND DIFFERENCES AMONG THE ANTI-CANCER DRUGS (DOSING PERIODS AND SIDE EFFECTS)?<br>·WHICH TREATMENT METHOD IS CHOSEN BY MANY OF THE PATIENTS?<br>·IF YOUR RELATIVE WAS A PATIENT, WHICH TREATMENT METHOD WOULD YOU CHOOSE? |
| I DON'T TRUST/LIKE THAT DOCTOR. IS HE [SHE] COMPETENT? | ·HOW MANY SURGERIES A YEAR DO YOU PERFORM?<br>·YOU ARE A MEDICAL INSTRUCTOR, AREN'T YOU?<br>·COULD I PLEASE REQUEST A FEMALE DOCTOR BECAUSE I'D BE EMBARRASSED? |
| THIS TREATMENT IS EXPENSIVE, ISN'T IT? | COULD YOU PLEASE PROVIDE AN EASY-TO-UNDERSTAND EXPLANATION OF THE MEDICAL EXPENSES THAT I MAY HAVE IF WE USE THIS NEW DRUG? |
| CHEMOTHERAPY TREATMENT IS STRENUOUS, ISN'T IT? | ·COULD YOU PLEASE CONSIDER TREATMENT METHODS WHILE PRIORITIZING ANTI-CANCER DRUGS THAT HAVE LESS SIDE EFFECTS?<br>·IF I HAVE STRONG SIDE EFFECTS, CAN I SWITCH TO AN ALTERNATIVE TREATMENT METHOD?<br>·IF WE CHOOSE HEAVY ION THERAPY OR RADIATION THERAPY, HOW MUCH LESS EFFECTIVE ARE THEY COMPARED TO OTHER TREATMENT METHODS? |
| WHY SHOULD I SUFFER FROM CANCER? | THE PATIENT DOES NOT HAVE MUCH MEDICAL KNOWLEDGE. COULD YOU PLEASE EXPLAIN ABOUT CANCER STATISTICS (ONE IN TWO PEOPLE HAS CANCER) AND TELL THE PATIENT THAT IT IS NOT HIS [HER] FAULT? |

FIG.11

| PRE-CONVERSION QUESTIONS | POST-CONVERSION QUESTIONS |
|---|---|
| I FEEL UNSTEADY ON MY LEGS. COULD YOU PLEASE PROVIDE A MEDICATION? (AN ELDERLY PATIENT WHO OCCASIONALLY VISITS THE HOSPITAL FOR SWOLLEN LEGS) | * TO INFORM THE PATIENT THAT SWOLLEN LEGS ARE THE CAUSE OF FEELING UNSTEADY, AND THERE IS LOW RISK OF ANEMIA OR STROKE.<br><br>DR. A (PRIMARY CARE DOCTOR WHO SPECIALIZES IN VASCULAR SURGERY):<br>THE SWELLING WORSENED AND MADE WALKING DIFFICULT. PLEASE PRESCRIBE MY REGULARLY MEDICATION.<br><br>DR. B (PART-TIME DOCTOR ON DUTY):<br>THE SWELLING OF MY LEGS WORSENED AND MADE WALKING DIFFICULT. PLEASE PRESCRIBE Y mg X (A DIURETIC) AS INDICATED IN THE CHART.<br>(THE DETAILS OF THE REGULAR TREATMENT ARE DESCRIBED.)<br><br>DR. C (MIDDLE-RANKED PHYSICIAN WHO IS NOT THE PRIMARY CARE DOCTOR):<br>THE SWELLING OF MY LEGS WORSENED AND MADE WALKING DIFFICULT. PLEASE PRESCRIBE THE DIURETIC.<br>(THE CAUSE OF THE PROBLEM IS DESCRIBED, BUT THE DETAILS OF THE TREATMENT ARE SIMPLIFIED.) |
| IS IT OK TO STOP TAKING THE WHITE PILLS? | IN THIS EXAMPLE, A WHITE FILM-COATED ANTI-BACTERIAL MEDICATION WAS PRESCRIBED A WEEK AGO TO TREAT A BLADDER INFECTION.<br><br>DR. A (PRIMARY CARE DOCTOR):<br>IS IT OK TO STOP TAKING X (THE NAME OF THE DRUG)?<br><br>DR. B (PART-TIME DOCTOR):<br>IS IT OK TO STOP TAKING X (THE NAME OF THE DRUG) WHICH WAS PRESCRIBED A WEEK AGO TO TREAT A BLADDER INFECTION?<br><br>DR. C (DIFFERENT DEPARTMENT):<br>IS IT OK TO STOP TAKING X (THE NAME OF THE DRUG) WHICH WAS PRESCRIBED TO TREAT A BLADDER INFECTION? |

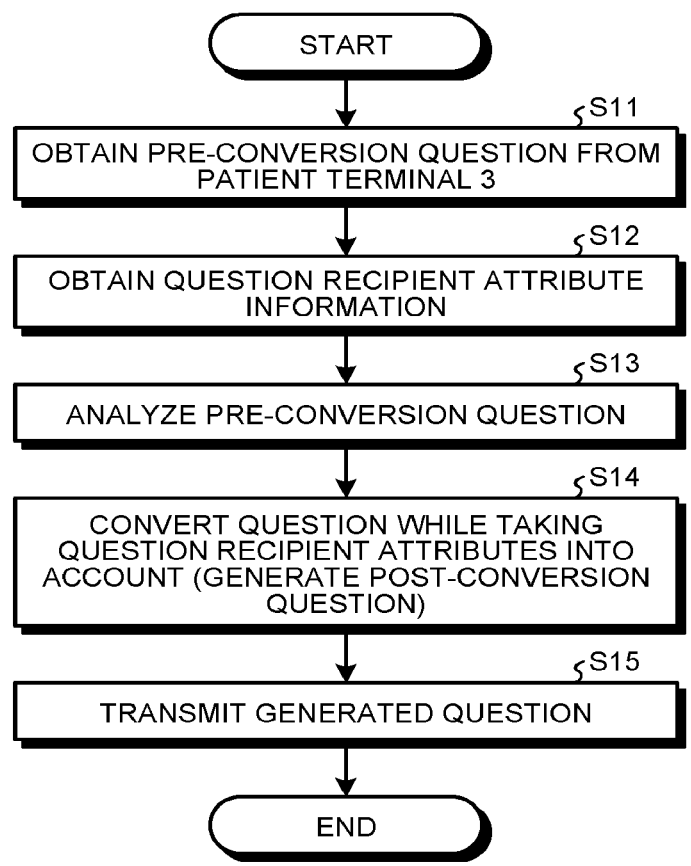

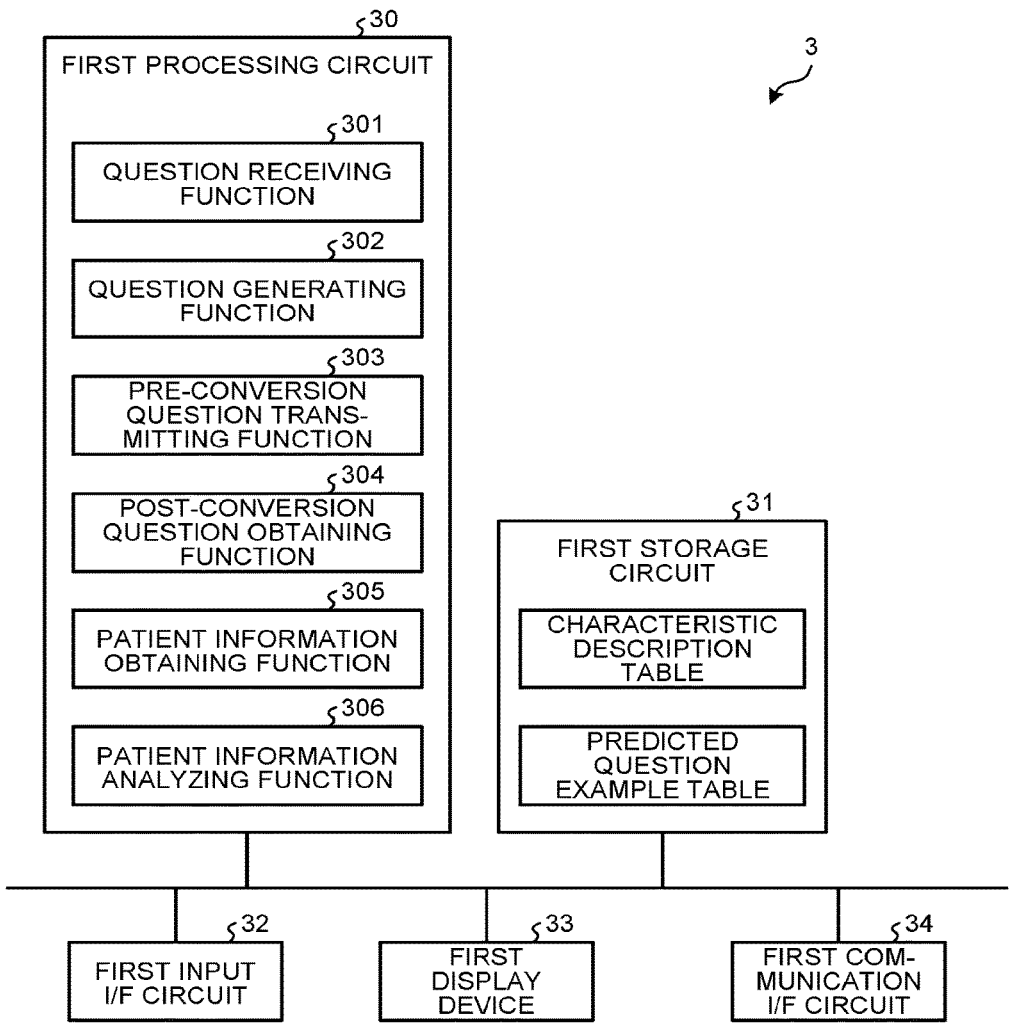

| MEDICAL INFORMATION RELATED TO PATIENT |
|---|
| PATIENT A: BREAST CANCER, FEMALE, AGE 40; HAS NO PREVIOUS MAJOR MEDICAL HISTORY; HER GRANDMOTHER AND MOTHER HAVE A HISTORY OF BREAST CANCER. |
| PATIENT B: FEMALE, AGE 50, RECURRENT BREAST CANCER. SHE HAD SURGERY, CHEMOTHERAPY, AND RADIATION THERAPY THREE YEARS AGO. |
| PATIENT C: MALE, AGE 70, DIABETES HAS DEVELOPED INTO DIABETIC NEPHROPATHY |
| PATIENT D: FEMALE, AGE 40, BREAST CANCER; DIAGNOSED AS STAGE 2 AND TRIPLE-NEGATIVE TYPE FROM TEST RESULTS; IMAGING TEST RESULTS SEEM TO EXHIBIT NO INFILTRATION. HAS NO PREVIOUS MAJOR MEDICAL HISTORY. HER GRANDMOTHER AND MOTHER HAVE A HISTORY OF BREAST CANCER. SHE HAS A HEALTH CHECK-UP EVERY YEAR. |

FIG.16

| INFORMATION RELATED TO ACTIVITIES OF PATIENT | SPECIFIC EXAMPLES | CHARACTERISTIC INFORMATION AND/OR MEDICAL INFORMATION TO BE CATEGORIZED |
|---|---|---|
| PURCHASE HISTORY OF INDIVIDUAL (PATIENT) | TOTAL PURCHASE AMOUNT PER MONTH | FINANCIAL CHARACTERISTICS |
| PURCHASE HISTORY OF INDIVIDUAL (PATIENT) | PURCHASE HISTORY OF NON-ESSENTIAL ITEMS; (ONLINE) LOTTERIES | PERSONALITY CHARACTERISTICS, RISK CHARACTERISTICS, FINANCIAL CHARACTERISTICS |
| PURCHASE HISTORY OF INDIVIDUAL (PATIENT) | PURCHASE HISTORY OF ALCOHOL, CIGARETTES, ETC. | MEDICAL INFORMATION, FINANCIAL CHARACTERISTICS, PERSONALITY CHARACTERISTICS, RISK CHARACTERISTICS, INNOVATIVE CHARACTERISTICS |
| PURCHASE HISTORY OF INDIVIDUAL (PATIENT) | PURCHASE HISTORY OF SECURITY GOODS | PERSONALITY CHARACTERISTICS, RISK CHARACTERISTICS, FINANCIAL CHARACTERISTICS |
| PURCHASE HISTORY OF INDIVIDUAL (PATIENT) | PAYMENT HISTORY AT RESTAURANTS | PERSONALITY CHARACTERISTICS, RISK CHARACTERISTICS, HEALTH CHARACTERISTICS, FAMILY CHARACTERISTICS, FINANCIAL CHARACTERISTICS |
| PURCHASE HISTORY OF INDIVIDUAL (PATIENT) | PURCHASE HISTORY OF HEALTH PRODUCTS AND SUPPLEMENTS | PERSONALITY CHARACTERISTICS, RISK CHARACTERISTICS, INNOVATIVE CHARACTERISTICS, HEALTH CHARACTERISTICS |
| PURCHASE HISTORY OF INDIVIDUAL (PATIENT) | PURCHASE HISTORY OF OVER-THE-COUNTER MEDICATIONS | INNOVATIVE CHARACTERISTICS, RISK CHARACTERISTICS, HEALTH CHARACTERISTICS |
| PURCHASE HISTORY OF INDIVIDUAL (PATIENT) | GYM VISIT HISTORY AND PURCHASE HISTORY OF HEALTH GOODS | PERSONALITY CHARACTERISTICS, RISK CHARACTERISTICS, INNOVATIVE CHARACTERISTICS, MEDICAL INFORMATION |
| PURCHASE HISTORY OF INDIVIDUAL (PATIENT) | PURCHASE HISTORY OF GASOLINE; HISTORY OF RELOADING FUNDS FOR TRANSPORTATION EXPENSES | PERSONALITY CHARACTERISTICS, RISK CHARACTERISTICS, INNOVATIVE CHARACTERISTICS |
| PURCHASE HISTORY OF INDIVIDUAL (PATIENT) | PURCHASE HISTORY OF HOME ELECTRIC APPLIANCES (AIR PURIFIER), WATER PURIFIER, AND CLEANING PRODUCTS | RISK CHARACTERISTICS, INNOVATIVE CHARACTERISTICS, PERSONALITY CHARACTERISTICS, HEALTH CHARACTERISTICS, FAMILY CHARACTERISTICS |
| PURCHASE HISTORY OF INDIVIDUAL (PATIENT) | PURCHASE HISTORY OF BOOKS (TITLES AND PRICES) | PERSONALITY CHARACTERISTICS, RISK CHARACTERISTICS, INNOVATIVE CHARACTERISTICS, FINANCIAL CHARACTERISTICS, MEDICAL LITERACY CHARACTERISTICS, FAMILY CHARACTERISTICS |
| PURCHASE HISTORY OF INDIVIDUAL (PATIENT) | PURCHASE HISTORY OF GROCERIES | PERSONALITY CHARACTERISTICS, RISK CHARACTERISTICS, FINANCIAL CHARACTERISTICS, MEDICAL INFORMATION, FAMILY CHARACTERISTICS |
| PURCHASE HISTORY OF INDIVIDUAL (PATIENT) | HISTORY OF NEW PRODUCTS (TYPES, FREQUENCY, AND HOW SOON AFTER MARKET RELEASE) | PERSONALITY CHARACTERISTICS, RISK CHARACTERISTICS, INNOVATIVE CHARACTERISTICS, FINANCIAL CHARACTERISTICS |
| PURCHASE HISTORY OF INDIVIDUAL (PATIENT) | PURCHASE HISTORY OF BEAUTY-RELATED PRODUCTS | PERSONALITY CHARACTERISTICS, RISK CHARACTERISTICS, INNOVATIVE CHARACTERISTICS, FINANCIAL CHARACTERISTICS |
| PURCHASE HISTORY OF INDIVIDUAL (PATIENT) | PURCHASE HISTORY OF CLOTHING | PERSONALITY CHARACTERISTICS, FINANCIAL CHARACTERISTICS, FAMILY CHARACTERISTICS |

FIG.17

| INFORMATION RELATED TO ACTIVITIES OF PATIENT | SPECIFIC EXAMPLES | CHARACTERISTIC INFORMATION AND/OR MEDICAL INFORMATION TO BE CATEGORIZED |
|---|---|---|
| WEB BROWSING HISTORY | WEB BROWSING HISTORY RELATED TO TREATMENT METHODS IN INNOVATIVE MEDICAL CARE | INNOVATIVE CHARACTERISTICS, MEDICAL LITERACY CHARACTERISTICS |
| WEB BROWSING HISTORY | WEB BROWSING HISTORY RELATED TO RISKS OF INNOVATIVE MEDICAL CARE | RISK CHARACTERISTICS, MEDICAL LITERACY CHARACTERISTICS |
| WEB BROWSING HISTORY | WEB BROWSING HISTORY RELATED TO TREATMENT EXPENSES OF INNOVATIVE MEDICAL CARE | FINANCIAL CHARACTERISTICS |
| WEB BROWSING HISTORY | WEB BROWSING HISTORY RELATED TO TREATMENT EXPENSES OF EACH OF DIFFERENT TREATMENT METHODS | FINANCIAL CHARACTERISTICS |
| WEB BROWSING HISTORY | WEB BROWSING HISTORY RELATED TO TREATMENT RESULTS | RISK CHARACTERISTICS, PERSONALITY CHARACTERISTICS, MEDICAL LITERACY CHARACTERISTICS |
| WEB BROWSING HISTORY | WEB BROWSING HISTORY RELATED TO HOSPITAL REPUTATIONS | CONGENIALITY CHARACTERISTICS, PERSONALITY CHARACTERISTICS |
| WEB BROWSING HISTORY | WHETHER THE PATIENT HAS A HISTORY OF BROWSING WEBSITES FOR SPECIALISTS OR WEBSITES FOR THE GENERAL PUBLIC | MEDICAL LITERACY CHARACTERISTICS |
| WEB BROWSING HISTORY | SEARCH HISTORY OF MEDICAL TERMS | MEDICAL LITERACY CHARACTERISTICS |
| WEB BROWSING HISTORY | RATIOS OF BROWSING VIEWS AND BROWSING DURATIONS BETWEEN MEDICAL WEBSITES AND OTHER SITES | PERSONALITY CHARACTERISTICS, RISK CHARACTERISTICS, INNOVATIVE CHARACTERISTICS, MEDICAL LITERACY CHARACTERISTICS |
| WEB BROWSING HISTORY | BROWSING HISTORY OF FOLK REMEDIES | PERSONALITY CHARACTERISTICS, RISK CHARACTERISTICS, INNOVATIVE CHARACTERISTICS, MEDICAL LITERACY CHARACTERISTICS |
| WEB BROWSING HISTORY | INFORMATION PREFERENCE (e.g., TYPES OF CATEGORIES OF NEWS) | PERSONALITY CHARACTERISTICS, RISK CHARACTERISTICS, INNOVATIVE CHARACTERISTICS, MEDICAL LITERACY CHARACTERISTICS, CONGENIALITY CHARACTERISTICS |

FIG.18

| INFORMATION RELATED TO ACTIVITIES OF PATIENT | SPECIFIC EXAMPLES | CHARACTERISTIC INFORMATION AND/OR MEDICAL INFORMATION TO BE CATEGORIZED |
|---|---|---|
| TWEETS (POSTS) ON SNS | "I'M GOING TO HAVE SURGERY SOON. I'M VERY NERVOUS". | PERSONALITY CHARACTERISTICS, MEDICAL LITERACY CHARACTERISTICS |
| TWEETS (POSTS) ON SNS | "I'M WORRIED IF I CAN PAY THE TREATMENT EXPENSES". | FINANCIAL CHARACTERISTICS, PERSONALITY CHARACTERISTICS |
| TWEETS (POSTS) ON SNS | "MY DOCTOR DOES NOT SPEAK VERY CANDIDLY. I WANT TO HAVE A DIFFERENT DOCTOR". | CONGENIALITY CHARACTERISTICS, PERSONALITY CHARACTERISTICS |
| TWEETS (POSTS) ON SNS | "I DON'T LIKE THAT MALE DOCTOR". | CONGENIALITY CHARACTERISTICS, PERSONALITY CHARACTERISTICS |
| TWEETS (POSTS) ON SNS | "I'M GOING TO HAVE SURGERY AND I TRUST MY DOCTOR". | CONGENIALITY CHARACTERISTICS, PERSONALITY CHARACTERISTICS |
| TWEETS (POSTS) ON SNS | "I REALLY HOPE TO HAVE A TREATMENT WITH THE LOWEST RISK". | RISK CHARACTERISTICS, PERSONALITY CHARACTERISTICS, INNOVATIVE CHARACTERISTICS |
| TWEETS (POSTS) ON SNS | "I WONDER WHO'S GOING TO TAKE CARE OF MY CHILDREN". | PERSONALITY CHARACTERISTICS, FINANCIAL CHARACTERISTICS, FAMILY CHARACTERISTICS |
| TWEETS (POSTS) ON SNS | THE NUMBER OF MEDICAL TERMS BEING USED | MEDICAL LITERACY CHARACTERISTICS |
| TWEETS (POSTS) ON SNS | THE RATIO BETWEEN SUBJECTS OF SENTENCES BEING SELF AND OTHERS | PERSONALITY CHARACTERISTICS |
| TWEETS (POSTS) ON SNS | THE RATIO BETWEEN POSITIVE WORDS AND NEGATIVE WORDS | PERSONALITY CHARACTERISTICS, RISK CHARACTERISTICS, INNOVATIVE CHARACTERISTICS |
| TWEETS (POSTS) ON SNS | THE NUMBER OF FOLK-REMEDY-RELATED WORDS BEING USED | PERSONALITY CHARACTERISTICS, RISK CHARACTERISTICS, INNOVATIVE CHARACTERISTICS |
| TWEETS (POSTS) ON SNS | THE NUMBER OF FOLLOWING AND FOLLOWERS ON SNS | PERSONALITY CHARACTERISTICS/ CONGENIALITY CHARACTERISTICS |
| TWEETS (POSTS) ON SNS | INTENSITY IN TONES OF EXPRESSIONS | PERSONALITY CHARACTERISTICS, CONGENIALITY CHARACTERISTICS |

FIG.19

| INFORMATION RELATED TO ACTIVITIES OF PATIENT | SPECIFIC EXAMPLES | CHARACTERISTIC INFORMATION AND/OR MEDICAL INFORMATION TO BE CATEGORIZED |
|---|---|---|
| INFORMATION RELATED TO ACTIVITIES IN DAILY LIFE, ETC. (e.g., ACTIVITY HISTORY FROM SMARTPHONE AND THE LIKE) | FACILITIES VISITED BY THE PATIENT. PLACES TO WHICH THE PATIENT TRAVELED. FACILITIES USED BY THE PATIENT ON A DAILY BASIS. TYPES OF FOOD THE PATIENT EATS AT RESTAURANTS. | FINANCIAL CHARACTERISTICS PERSONALITY CHARACTERISTICS INNOVATIVE CHARACTERISTICS HEALTH CHARACTERISTICS |
| INFORMATION RELATED TO ACTIVITIES IN DAILY LIFE, ETC. (e.g., ACTIVITY HISTORY FROM SMARTPHONE AND THE LIKE) | AT WHAT TIME THE PATIENT HAS MEALS. HOW LONG THE PATIENT SLEEPS. TIME AT WHICH THE PATIENT GETS UP. | HEALTH CHARACTERISTICS, PERSONALITY CHARACTERISTICS, MEDICAL LITERACY CHARACTERISTICS |
| INFORMATION RELATED TO ACTIVITIES IN DAILY LIFE, ETC. (e.g., ACTIVITY HISTORY FROM SMARTPHONE AND THE LIKE) | INTENSITIES OF VERBAL AND WRITTEN LANGUAGE | PERSONALITY CHARACTERISTICS, CONGENIALITY CHARACTERISTICS |

FIG.20

| INFORMATION RELATED TO ACTIVITIES OF PATIENT | SPECIFIC EXAMPLES | CHARACTERISTIC INFORMATION AND/OR MEDICAL INFORMATION TO BE CATEGORIZED |
|---|---|---|
| INFORMATION THAT CAN BE OBTAINED FROM IT DEVICES (FAMILY STRUCTURE) | IS MARRIED AND HAS TWO CHILDREN | FINANCIAL CHARACTERISTICS |
| INFORMATION THAT CAN BE OBTAINED FROM IT DEVICES (OCCUPATION) | OCCUPATION: COMPANY EMPLOYEE | FINANCIAL CHARACTERISTICS |
| INFORMATION THAT CAN BE OBTAINED FROM IT DEVICES (INCOME) | ANNUAL INCOME: *** YEN | FINANCIAL CHARACTERISTICS |
| INFORMATION THAT CAN BE OBTAINED FROM IT DEVICES (COMMUTE TO WORK) | COMMUTING TIME AND MEANS | FINANCIAL CHARACTERISTICS, PERSONALITY CHARACTERISTICS |

FIG.21

| INFORMATION RELATED TO ACTIVITIES OF PATIENT | SPECIFIC EXAMPLES | CHARACTERISTIC INFORMATION AND/OR MEDICAL INFORMATION TO BE CATEGORIZED |
|---|---|---|
| INFORMATION RELATED TO HEALTH, PHYSICAL CHARACTERISTICS, ETC. (e.g., VITAL INFORMATION OBTAINED FROM WEARABLE MEASURING DEVICES AND THE LIKE) | BLOOD PRESSURE HEARTRATE ELECTROCARDIOGRAMS BLOOD OXYGEN SATURATION (SpO2) | MEDICAL INFORMATION |
| INFORMATION RELATED TO HEALTH, PHYSICAL CHARACTERISTICS, ETC. (e.g., VITAL INFORMATION OBTAINED FROM WEARABLE MEASURING DEVICES AND THE LIKE) | THE NUMBER OF WALKING STEPS ACCELERATION (EXERCISE AMOUNT PER DAY: EXERCISE INTENSITY AND DURATION) | MEDICAL INFORMATION PERSONALITY CHARACTERISTICS |
| INFORMATION RELATED TO HEALTH, PHYSICAL CHARACTERISTICS, ETC. (e.g., VITAL INFORMATION OBTAINED FROM WEARABLE MEASURING DEVICES AND THE LIKE) | HEIGHT WEIGHT BODY FAT ABDOMINAL CIRCUMFERENCE SUBCUTANEOUS FAT THICKNESS | MEDICAL INFORMATION |
| INFORMATION RELATED TO HEALTH, PHYSICAL CHARACTERISTICS, ETC. (e.g., VITAL INFORMATION OBTAINED FROM WEARABLE MEASURING DEVICES AND THE LIKE) | BLOOD SUGAR | MEDICAL INFORMATION |
| INFORMATION RELATED TO HEALTH, PHYSICAL CHARACTERISTICS, ETC. (e.g., VITAL INFORMATION OBTAINED FROM WEARABLE MEASURING DEVICES AND THE LIKE) | RESPIRATION BODY MOVEMENTS SNORING NOISE | MEDICAL INFORMATION |

FIG.22

| TYPES OF CHARACTERISTICS | DESCRIPTION |
|---|---|
| INNOVATIVE CHARACTERISTICS | · HAS A TENDENCY TO LIKE/DISLIKE STANDARD MEDICAL CARE.<br>· HAS A TENDENCY TO LIKE INNOVATIVE MEDICAL CARE (e.g., WHETHER THE PATIENT WOULD LIKE TO RECEIVE TREATMENT WITH A SURGICAL ROBOT OR TO HAVE NORMAL ENDOSCOPY SURGERY). |
| RISK CHARACTERISTICS | · HAS A TENDENCY TO AVOID/ACCEPT RISKS (e.g., WHETHER THE PATIENT WISHES TO TAKE AN ANTI-CANCER DRUG THAT HAS SIDE EFFECTS, BUT IS HIGHLY EFFICIENT).<br>· IS NONCHALANT ABOUT RISKY SITUATIONS (e.g., UNDERGOING COSMETIC SURGERY OR HAVING HIS [HER] TONGUE PIERCED). |
| FINANCIAL CHARACTERISTICS | · HAS A HIGH INCOME, HAS CANCER INSURANCE, HAS NEVER BEEN MARRIED, AND HAS NO CHILDREN.<br>· IS FROM A TWO-INCOME FAMILY WITH A MEDIUM-RANGE INCOME. HAS CANCER INSURANCE. HAS ONE CHILD (A 4-YEAR-OLD GOING TO KINDERGARTEN).<br>· LIVES ALONE ON PENSION. HAS NO RELATIVES NEARBY. |
| PERSONALITY CHARACTERISTICS | · HAS A CAUTIOUS AND QUIET PERSONALITY; IS INTROVERTED AND RETICENT.<br>· HAS AN OUTGOING PERSONALITY, LIKES NOVEL THINGS, AND IS EXTRAVAGANT.<br>· HAS AN ANALYTICAL PERSONALITY AND PREFERS LOGICAL THINKING AND COMMUNICATION.<br>· IS IMPATIENT AND OFTEN JUMPS TO WRONG CONCLUSIONS.<br>· HAS AN AGREEABLE PERSONALITY AND TENDS TO MAKE UP HIS [HER] MIND BY REFERRING TO OTHER PEOPLE'S OPINIONS AND BEHAVIORS. |
| CONGENIALITY CHARACTERISTICS | · IS REQUESTING A FEMALE DOCTOR<br>· IS REQUESTING A DOCTOR WHO CAN GIVE COMPASSIONATE AND DETAILED EXPLANATIONS.<br>· IS REQUESTING A DOCTOR WHO CAN PROVIDE GUIDANCE BY RECOMMENDING TREATMENT METHODS, ETC. |
| MEDICAL LITERACY CHARACTERISTICS | · IS NOT ABLE TO UNDERSTAND MEDICAL TERMS AT ALL.<br>· HAS RESEARCHED LOTS OF MEDICAL INFORMATION<br>· HAS A FAMILY MEMBER WORKING AS A NURSE AND HAS SOME MEDICAL KNOWLEDGE<br>· HAS RECEIVED HIGHER EDUCATION<br>· IS A MEDICAL PROVIDER |

FIG.23

| TYPES OF CHARACTERISTICS | DESCRIPTION |
|---|---|
| INNOVATIVE CHARACTERISTICS | THE PATIENT IS A VERY CAREER-ORIENTED WOMAN WHO WAS THE FIRST FEMALE TO BE PROMOTED TO MANAGER IN THE COMPANY. SHE IS FULL OF MOTIVATION TO BE AHEAD OF HER TIME AND HAS LOTS OF CURIOSITY. |
| RISK CHARACTERISTICS | SHE HAS A PROGRESSIVE PERSONALITY BUT LIKES TO PROCEED STEADILY AND SAFELY. SHE IS CURRENTLY THE LEADER OF A NEW PROJECT AT WORK AND IS HIGHLY MOTIVATED TO MAKE THE PROJECT SUCCESSFUL. FROM HER TWEETS ON SNS, IT IS UNDERSTOOD THAT THE PROJECT IS ONE OF THE HIGHEST PRIORITIES IN HER LIFE RIGHT NOW. |
| FINANCIAL CHARACTERISTICS | SHE HAS A HIGH INCOME AND HAS CANCER INSURANCE. SHE OFTEN EATS OUT RATHER THAN COOKING AT HOME. SHE ALSO FREQUENTLY DINES AT EXPENSIVE RESTAURANTS. |
| PERSONALITY CHARACTERISTICS | SHE IS SOCIALLY VERY ACTIVE, BUT FEELS LONELY. SHE LIKES TO PROCEED STEADILY AND LABORIOUSLY. SHE HAS NOT TWEETED ABOUT HAVING BREAST CANCER ON SNS. |
| CONGENIALITY CHARACTERISTICS | SHE IS REQUESTING A FEMALE DOCTOR, SINCE THE DISEASE IS GENDER-SENSITIVE. ALSO, SHE IS REQUESTING A DOCTOR WHO CAN COMPASSIONATELY GIVE ADVICE AND PROVIDE DETAILED EXPLANATIONS. |
| MEDICAL LITERACY CHARACTERISTICS | SHE HAS RESEARCHED ON THE INTERNET ABOUT STANDARD BREAST CANCER TREATMENTS. SHE READ ABOUT MANY OTHER PATIENTS' EXPERIENCES ON BREAST CANCER PATIENTS' SNS WEBSITES. SHE SEARCHED IN MANY FOLK REMEDY WEBSITES WHERE PEOPLE CLAIM THAT CANCER WAS CURED WITHOUT SURGERY. SHE ASKED QUESTIONS ON BREAST CANCER SNS WEBSITES. SHE ALSO SENT INQUIRY EMAILS TO MEDICAL FACILITIES OFFERING FOLK REMEDIES. |
| HEALTH CHARACTERISTICS | FEMALE, AGE: 40. HEIGHT: 165 cm. WEIGHT: 47 kg. SHE IS IN GOOD HEALTH. SHE HAS NO HABITS OF SMOKING OR DRINKING ALCOHOL. SHE HAS NO HABIT OF EXERCISING REGULARLY. SHE USUALLY SLEEPS FOR 5 HOURS, BUT SLEEPS LONGER ON WEEKENDS TO COMPENSATE. |
| FAMILY CHARACTERISTICS | SHE HAS NEVER BEEN MARRIED AND HAS NO CHILDREN. SHE IS THE YOUNGER OF TWO DAUGHTERS. SHE IS ORIGINALLY FROM A RURAL AREA AND HAS NO RELATIVES NEARBY. |

FIG.24

| EXAMPLES OF AUTOMATICALLY-GENERATED QUESTIONS |
| --- |
| WHY DO I HAVE BREAST CANCER? |
| AM I GOING TO DIE? |
| I FEEL FULFILLED WITH MY WORK RIGHT NOW, AND I DON'T WANT TO START THE TREATMENT. (WOULD IT BE POSSIBLE TO POSTPONE THE TREATMENT?) |
| CAN I BE TREATED WITH A FOLK REMEDY (CANCER FIGHTING MUSHROOMS)? |
| IS THERE A TREATMENT METHOD WITHOUT SURGERY? |
| I'D LIKE TO KEEP WORKING AND HAVE TREATMENT. |
| I'M AWARE THAT EXPENSES ARE HIGHER, BUT CAN I HAVE INNOVATIVE MEDICAL CARE (HEAVY ION THERAPY OR IMMUNE THERAPY)? |
| I'D LIKE TO HAVE A SECOND OPINION. |
| I'D LIKE TO HAVE AN EASY-TO-UNDERSTAND MEDICAL EXPLANATION OF THE TREATMENT METHOD RECOMMENDED BY THE DOCTOR. |

FIG.25

| EXAMPLES OF AUTOMATICALLY-GENERATED QUESTIONS |
| --- |
| A QUESTION FROM A WORRYWART PATIENT WITH NO MEDICAL KNOWLEDGE: PLEASE PROVIDE AN EASY-TO-UNDERSTAND EXPLANATION OF THE SIDE EFFECTS THAT MAY BE EXPERIENCED IF THE NEW DRUG IS USED. |
| A QUESTION FROM A PATIENT WITH A LOW FINANCIAL CAPABILITY AND NO MEDICAL KNOWLEDGE: PLEASE PROVIDE AN EASY-TO-UNDERSTAND EXPLANATION OF THE MEDICAL EXPENSES FOR THE NEW DRUG. |
| A QUESTION FROM A PATIENT HAVING MEDICAL KNOWLEDGE AND A TENDENCY TO ACCEPT RISKS: I HEARD THERE IS A NEW DRUG CALLED YZ FOR THIS DISEASE. HOW EFFECTIVE IS THIS DRUG FOR MY SYMPTOMS? |
| A QUESTION FROM A PATIENT HAVING MEDICAL KNOWLEDGE AND A TENDENCY TO NOT ACCEPT INNOVATIVE CARE: THIS TREATMENT METHOD HAS SIDE EFFECTS LIKE YZ. WOULD IT BE POSSIBLE TO NOT USE THIS METHOD? |
| A QUESTION FROM A PATIENT WHO HAS NO MEDICAL KNOWLEDGE AND IS IMPATIENT HOW LONG WILL IT TAKE TO BE CURED? |
| A PATIENT WHO HAD AN ARGUMENT WITH DR. XX CAN I HAVE AN APPOINTMENT ON A DAY WHEN DR. XX IS OUT OF THE OFFICE? |
| A PATIENT WHO IS TAKING AN ANTICOAGULANT DRUG AND PREFERS INNOVATIVE TREATMENTS: WHY CAN'T I HAVE ROBOT SURGERY RIGHT AWAY? |
| A PATIENT WHO HAS TENDENCY TO ACCEPT INNOVATIVE CARE, IS A WORRYWART, AND MAY HAVE BREAST CANCER: IS IT A GOOD IDEA TO TAKE A GENETIC TEST? |

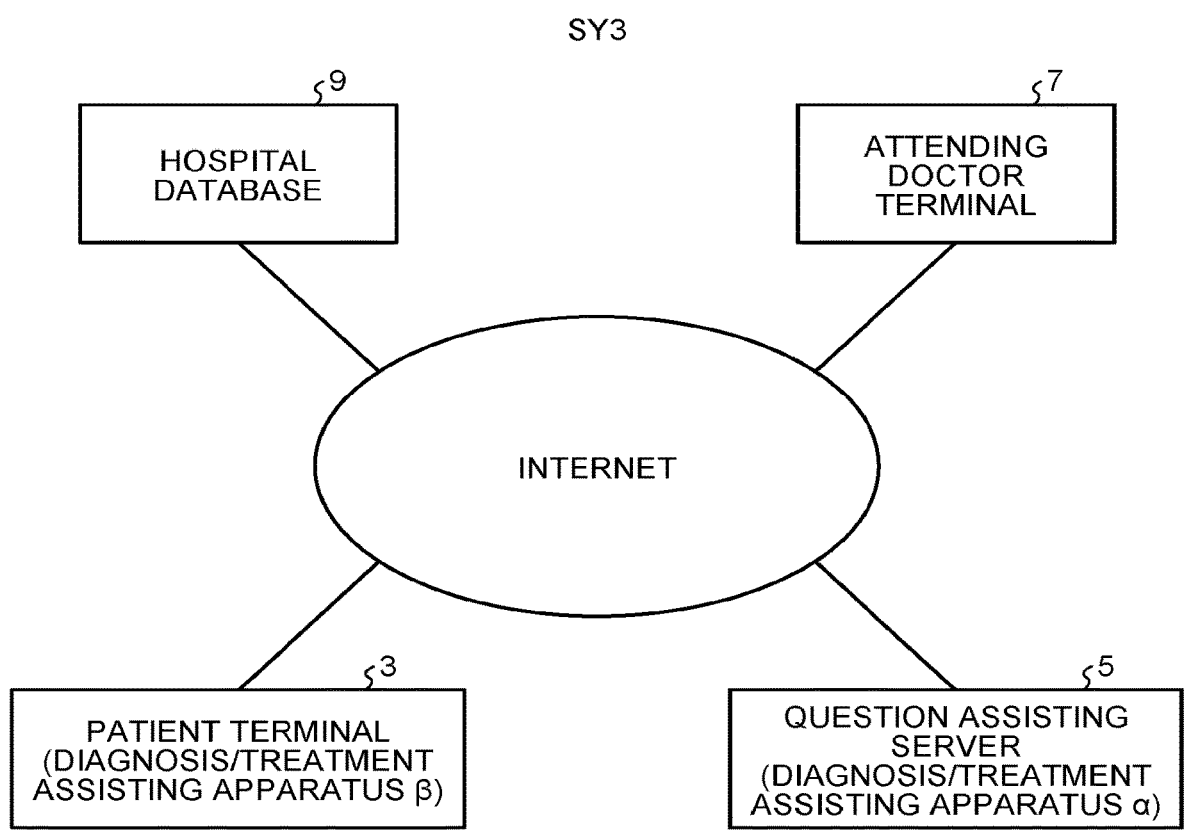

DIAGNOSIS/TREATMENT ASSISTING APPARATUS AND DIAGNOSIS/TREATMENT ASSISTING SYSTEM

CROSS-REFERENCE TO RELATED APPLICATIONS

This application is based upon and claims the benefit of priority from Japanese Patent Application No. 2019-175982, filed on Sep. 26, 2019; the entire contents of which are incorporated herein by reference.

FIELD

Embodiments described herein relate generally to a diagnosis and/or treatment (hereinafter, "diagnosis/treatment") assisting apparatus and a diagnosis/treatment assisting system.

BACKGROUND

Conventionally, before surgery and the like, informed consent is carried out during which a medical doctor (hereinafter, "doctor") explains the condition of a disease and treatment methods, as well as risks of treatment and the like, to the patient and his/her family. As for the explanation by the doctor, an explanatory document in the form of printed text is usually handed to the patient and his/her family. After an oral explanation by the doctor, questions and answers are exchanged.

For example, when the disease is breast cancer, the explanation provided for the patient during an informed consent process is limited to basic information related to the condition of the disease, treatment methods, and medical risks such as complications, as well as postoperative instructions and schedules. Further, for serious diseases such as cancers, strokes, and heart diseases, there are hospitals, online medical information providing websites, and the like prepared with Frequently Asked Questions (FAQs) that explain matters about which patients and their families frequently demand information, regarding an outline of surgery and risks involved in surgery while using charts, tables, and the like. Because the information provided in the FAQs is also limited to general information, suitability of treatment methods and the like are determined after each patient consults with a doctor individually.

Further, when informed consent is carried out, generally speaking, it seems difficult for patients and their families to calmly listen to doctors' explanations, because of the state of mind and scarcity of medical knowledge.

BRIEF DESCRIPTION OF THE DRAWINGS

FIG. 1 is a diagram illustrating an exemplary configuration of a diagnosis/treatment assisting system according to a first embodiment;

FIG. 2 is a diagram for explaining an exemplary configuration of a patient terminal;

FIG. 3 illustrates an example of a list of pre-conversion questions generated by a question generating function;

FIG. 6 is a table illustrating examples indicating how the pre-conversion questions in FIG. 3 have been converted into post-conversion questions represented by "questions using expressions (mild expressions) that are polite and pay attention to subtleties";

FIG. 7 is a table illustrating examples indicating how the pre-conversion questions in FIG. 4 have been converted into post-conversion questions represented by "questions using medically appropriate expressions";

FIG. 11 is a table illustrating examples indicating how pre-conversion questions have been converted into post-conversion questions by using attribute information and an expression conversion table including question recipient attributes;

FIG. 12 is a flowchart illustrating an example of a flow in a question converting process performed by a question assisting server that serves as a diagnosis/treatment assisting apparatus according to a first modification example;

FIG. 14 is a diagram for explaining an exemplary configuration of a patient terminal in the diagnosis/treatment assisting system according to the second embodiment;

FIG. 15 is a table illustrating an example of medical information related to patients, for each of the patients;

FIG. 16 is a table illustrating examples of information related to activities of a patient of which characteristics are categorized;

FIG. 17 is a table illustrating other examples of the information related to activities of the patient of which characteristics are categorized;

FIG. 18 is a table illustrating more examples of the information related to activities of the patient of which characteristics are categorized;

FIG. 19 is a table illustrating more examples of the information related to activities of the patient of which characteristics are categorized;

FIG. 20 is a table illustrating more examples of the information related to activities of the patient of which characteristics are categorized;

FIG. 21 is a table illustrating more examples of the information related to activities of the patient of which characteristics are categorized;

FIG. 22 is a table for explaining examples of analysis results obtained by a patient information analyzing function;

FIG. 23 is a table for explaining other examples of analysis results obtained by the patient information analyzing function;

FIG. 24 is a table for explaining examples of questions automatically generated by the question generating function;

FIG. 25 is a table for explaining other examples of questions automatically generated by the question generating function;

FIG. 27 is a diagram illustrating an exemplary configuration of a diagnosis/treatment assisting system according to a third embodiment.

DETAILED DESCRIPTION

Figures 4, 5:
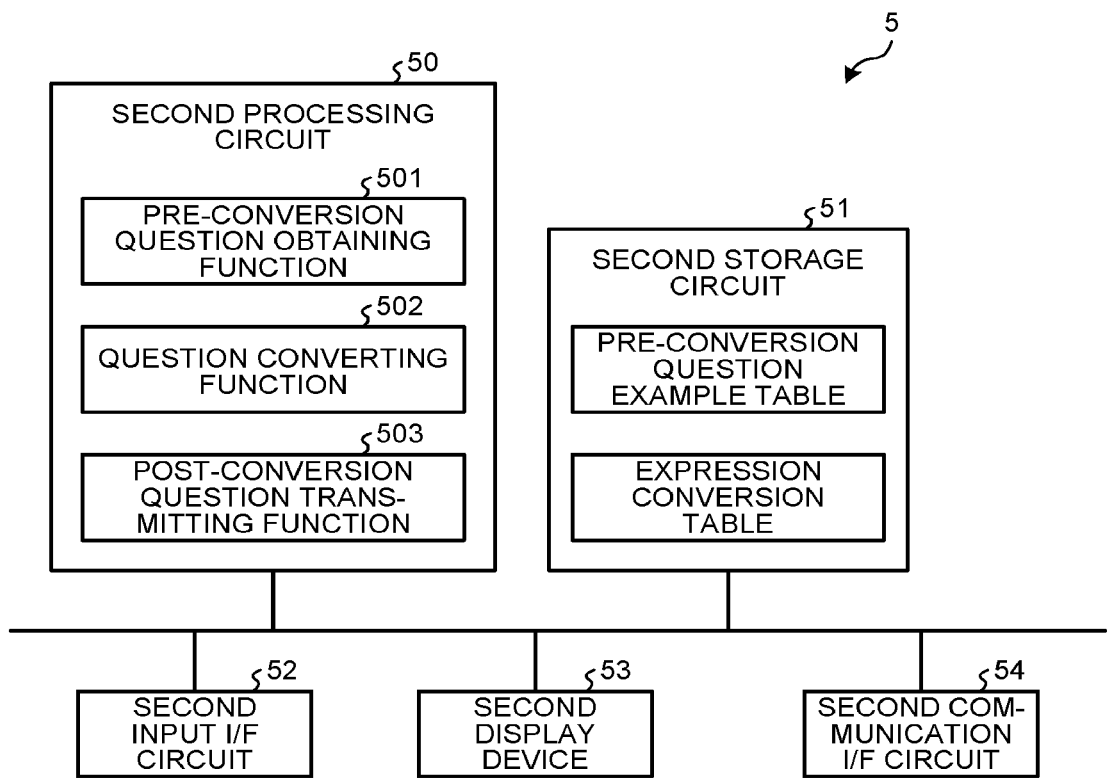
FIG. 4 illustrates another example of a list of pre-conversion questions generated by the question generating function.
FIG. 5 is a diagram for explaining an exemplary configuration of a question assisting server.

A diagnosis assisting apparatus according to an embodiment includes a processing circuit and a display circuit. The processing circuit is configured to obtain a first question represented by a question from a patient to a medical doctor. The processing circuit is configured to analyze content of the obtained first question. The processing circuit is configured to convert the first question into a second question having equivalent content and using a different expression, on the basis of a result of the analysis. The display circuit is configured to display the second question.

Exemplary embodiments will be explained below with reference to the accompanying drawings. In the following explanations, some of the constituent elements that have substantially the same functions or configurations will be referred to by using the same reference characters, and duplicated explanations will be provided only when necessary. Further, it is possible to combine any of the embodiments with other configurations or conventional techniques so long as no conflict occurs in the configurations.

First Embodiment

FIG. 1 is a diagram illustrating an exemplary configuration of a diagnosis/treatment assisting system SY1 according to a first embodiment. As illustrated in FIG. 1, the diagnosis/treatment assisting system SY1 according to the present embodiment includes a terminal on a patient's side (hereinafter, "patient terminal") 3, a question assisting server 5, a terminal on an attending doctor's side (hereinafter "attending doctor terminal") 7, and a hospital database 9. Each of the devices is capable of communicating with the other devices via the Internet.

The hospital database 9 is installed in a hospital, for example, and is configured to obtain and store therein medical information of each patient, from a Hospital Information System (HIS), a Radiology Information System (RIS), a Picture Archiving and Communication System (PACS), and/or the like.

Next, configurations of the patient terminal 3, the question assisting server, and the attending doctor terminal 7 will each be explained in detail.

The Patient Terminal 3

The patient terminal 3 is an information processing apparatus configured to receive questions of choice from a patient or his/her family, when a doctor gives explanations to the patient while carrying out informed consent or the like. Typically, the patient terminal 3 is a mobile phone (which may be a smartphone), a personal computer (which may be of a tablet type), or the like owned by the patient. In the following sections, to explain specific examples, a situation will be explained in which the patient himself/herself asks the doctor questions, while informed consent is carried out.

FIG. 2 is a diagram for explaining an exemplary configuration of the patient terminal 3. As illustrated in FIG. 2, the patient terminal 3 includes a first processing circuit 30, a first storage circuit 31, a first input interface (I/F) circuit 32, a first display device 33, and a first communication I/F circuit 34.

The first processing circuit 30 is a processor represented by a CPU configured to control entire processes of the patient terminal 3. For example, in response to an input operation received from an operator via the first input I/F circuit 32, the first processing circuit 30 is configured to control constituent elements of the patient terminal 3. Further, for example, the first processing circuit 30 is configured to control the first display device 33 so as to display various types of data stored in the first storage circuit 31, a GUI used for performing various types of input processes, results of computing processes, and the like.

Further, the first processing circuit 30 includes a question receiving function 301, a question generating function 302, a pre-conversion question transmitting function 303, and a post-conversion question obtaining function 304.

When the doctor gives explanations to the patient while carrying out informed consent or the like, the question receiving function 301 is configured to receive an instruction for a question converting process, a direct input of questions which the patient wishes to ask the doctor, a selection made on questions, and conditions and keywords to be used for generating questions.

The question generating function 302 is configured to generate the questions which the patient wishes to ask the doctor, on the basis of the information input via the question receiving function 301 and medical information related to the patient obtained from the hospital database 9. The questions generated by the question generating function 302 may be questions that are directly input in accordance with operations performed by the patient himself/herself or may be questions that are selected or generated on the basis of the conditions and keywords received by the question receiving function 301 so as to be used for generating the questions.

For example, when information such as "female", "breast cancer", "has no children", "is in her 30's", and "does not wish to have mastectomy" has been input via the question receiving function 301, the question generating function 302 is configured to transmit the information to the question assisting server 5 via the Internet. The question generating function 302 is configured to receive, from the question assisting server 5, question candidates extracted on the basis of the transmitted information and to cause the first display device 33 to display the question candidates. The question generating function 302 is configured to interactively prompt the patient to select desirable questions from among the displayed list of the question candidates. By using the first input I/F circuit 32, the patient is also able to further edit the questions which he/she selected.

In the present example, the questions generated by the question generating function 302 are questions prior to a converting process (explained later), these questions may be referred to as "pre-conversion questions".

Alternatively, the question generating function 302 may generate the questions by using an Artificial Intelligence (AI) model (e.g., a Deep Neural Network [DNN]) configured to receive an input of the information entered via the question receiving function 301 and the medical information related to the patient obtained from the hospital database 9 and to output questions which the patient wishes to ask the doctor. In that situation, the AI model is generated by using training-purpose data in which the various types of information entered by the patient and the medical information obtained from the hospital database 9 serve as input data, whereas the "questions" serve as training data.

FIG. 3 illustrates an example of a list of pre-conversion questions generated by the question generating function 302. FIG. 4 illustrates another example of a list of pre-conversion questions generated by the question generating function 302. As illustrated in FIGS. 3 and 4, the pre-conversion questions were created by the patient himself/herself having little medical knowledge and are not supposed to be sent to doctors without being converted. For this reason, the questions candidly express the current feelings of the patient and are expressed freely.

The pre-conversion question transmitting function 303 is configured to transmit the questions (the pre-conversion questions) generated by the question generating function 302, to the question assisting server via the first communication I/F circuit 34.

The post-conversion question obtaining function 304 is configured to obtain questions (post-conversion questions) resulting from a conversion performed by the question assisting server, from the question assisting server via the first communication I/F circuit 34.

In this situation, the question receiving function 301, the question generating function 302, the pre-conversion question transmitting function 303, and the post-conversion question obtaining function 304 are realized as a result of the first processing circuit 30 (i.e., the CPU) executing a controlling program. However, possible embodiments are not limited to this example, and it is also acceptable to realize a part or all of the question receiving function 301, the question generating function 302, the pre-conversion question transmitting function 303, and the post-conversion question obtaining function 304, by using dedicated hardware designed to execute the same functions, such as a semiconductor integrated circuit (e.g., an Application Specific Integrated Circuit [ASIC], a Digital Signal Processor [DSP], or a Field Programmable Gate Array [FPGA]), a conventional circuit module, or the like.

The first storage circuit 31 is connected to the first processing circuit 30 and has stored therein a dedicated program or the like used for generating questions (explained later). For example, the first storage circuit 31 is realized by using a semiconductor memory element such as a Random Access Memory (RAM) or a flash memory, or a hard disk, an optical disk, or the like.

The first input I/F circuit 32 is connected to the first processing circuit 30 and is configured to convert input operations received from the operator into electrical signals and to output the electrical signals to the first processing circuit 30. For example, the first input I/F circuit 32 is realized by using a trackball, a switch button, a mouse, a keyboard, a touch panel, and/or the like.

The first display device 33 is connected to the first processing circuit 30 and is configured to display various types of information and various types of image data output from the first processing circuit 30. For example, the first display device 33 is realized by using a liquid crystal monitor, a Cathode Ray Tube (CRT) monitor, a touch panel, or the like.

The first communication I/F circuit 34 is connected to the first processing circuit 30 and is configured to control the transfer of various types of data and communication that are performed with the question assisting server, the attending doctor terminal 7, and the hospital database 9. For example, the first communication I/F circuit 34 is configured to receive the various types of data from the question assisting server and the hospital database 9 and to output the received data to the first processing circuit 30. For example, the first communication I/F circuit 34 is realized by using a network card, a network adaptor, a Network Interface Controller (NIC), or the like.

The Question Assisting Server 5

When the doctor gives explanations to the patient while carrying out informed consent or the like, the question assisting server 5 is configured to receive the questions of choice created by the patient from the patient terminal 3 and to automatically convert the received questions into "questions using more appropriate expressions". The question assisting server 5 is a server provided by a service provider and is, for example, an information processing apparatus (a computer) installed in a cloud. The question assisting server 5 is configured to automatically transmit the questions resulting from the conversion (which may be referred to as "post-conversion questions"), to the patient terminal 3 and to the attending doctor terminal 7 with predetermined timing.

In this situation, the term "questions using more appropriate expressions" denotes "questions using medically appropriate expressions" or "questions using expressions (mild expressions) that are polite and pay attention to subtleties".

FIG. 5 is a diagram for explaining an exemplary configuration of the question assisting server 5. As illustrated in FIG. 5, the question assisting server 5 includes a second processing circuit 50, a second storage circuit 51, a second input I/F circuit 52, a second display device 53, and a second communication I/F circuit 54.

The second storage circuit 51 is connected to the second processing circuit 50 and has stored therein a dedicated program used for converting questions (explained later), and the like.

Further, the second storage circuit 51 has stored therein a pre-conversion question example table (a pre-conversion question example database). The pre-conversion question example table is a searchable database in which pre-conversion questions generated in the past and anticipated pre-conversion questions generated in advance are categorized according to medical cases, gender, age, family structures, treatment plans, and the like. By using the pre-conversion question example table, it is possible to extract the pre-conversion questions serving as the candidates, on the basis of the conditions and keywords received from the patient.

Further, the second storage circuit 51 has stored therein, in advance, an expression conversion table (an expression conversion database) used for converting "questions using expressions that are not yet appropriate" into "questions using more appropriate expressions". The expression conversion table is a table keeping pre-conversion questions freely created by patients in correspondence with post-conversion questions represented by questions using more appropriate expressions, for each of various types of question patterns. For example, the expression conversion table keeps a pre-conversion question such as "I don't want to have surgery. (Can I do something else?)" in correspondence with post-conversion questions such as "What would be the medical disadvantages if I don't have this treatment? I don't want to suffer from the side effects of anti-cancer drugs.", "How much will the treatment cost? I'm worried about the expenses.", and "Could you please refer me to a facility that offers treatment in my neighborhood?". By referring to the expression conversion table, it is possible to convert the pre-conversion question into the questions using the more appropriate expressions.

As for the second storage circuit 51, for example, the second storage circuit 51 is realized by using a semiconductor memory element such as a Random Access Memory (RAM) or a flash memory, or a hard disk, an optical disk, or the like.

The second processing circuit 50 is a processor represented by a CPU configured to control the entire processes of the question assisting server. The second processing circuit 50 includes a pre-conversion question obtaining function 501, a question converting function 502, and a post-conversion question transmitting function 503.

The pre-conversion question obtaining function 501 is configured to obtain a first question represented by a question from the patient to the doctor. In other words, the pre-conversion question obtaining function 501 is configured to obtain the pre-conversion question transmitted from the patient terminal 3. The pre-conversion question obtaining function 501 is configured to extract, from the pre-conversion question example table, pre-conversion questions serving as candidates, on the basis of the conditions and keywords such as "female", "breast cancer", "has no children", "is in her 30's", and "does not wish to have mastectomy" that were received from the patient terminal 3. The pre-conversion question obtaining function 501 is configured to transmit the extracted pre-conversion questions to the patient terminal 3 via the Internet.

The question converting function 502 corresponds to a first analyzing unit and a converting unit and is configured to analyze the content of the obtained pre-conversion question represented by the first question and to convert the pre-conversion question into a second question having equivalent content and using a different expression on the basis of a result of the analysis. In this situation, the analysis performed by the question converting function 502 is to determine which of the pre-conversion questions registered in advance in the expression conversion table is applicable, on the basis of the expressions contained in the pre-conversion question. For example, by referring to the expression conversion table stored in the second storage circuit 51 in advance, the question converting function 502 is configured to convert the pre-conversion question transmitted from the patient terminal 3, into a post-conversion question represented by a question using a more appropriate expression (generating the post-conversion question).

FIG. 6 is a table illustrating examples indicating how the pre-conversion questions in FIG. 3 have been converted into post-conversion questions represented by "questions using expressions (mild expressions) that are polite and pay attention to subtleties". For example, as illustrated in FIG. 6, on the basis of an analysis result, the pre-conversion question "This doctor seems unreliable. Can I trust this doctor?" has been converted into a post-conversion question having equivalent content and using a different expression such as "I'd like to have the surgery with an experienced doctor. Would it be possible to request the doctor who is the head of the department?".

Supposedly, if the patient asked the attending doctor the pre-conversion question "This doctor seems unreliable. Can I trust this doctor?" without any conversion, the question would be very impolite for the doctor. Also, the patient might find it difficult to ask because the question would be impolite, although the question contains his/her genuine feelings. Conversely, the post-conversion question such as "I'd like to have the surgery with an experienced doctor. Would it be possible to request the doctor who is the head of the department?" is not an impolite question for the attending doctor, and the patient is also able to ask a question reflecting his/her wishes.

FIG. 7 is a table illustrating examples indicating how the pre-conversion questions in FIG. 4 have been converted into post-conversion questions represented by "questions using medically appropriate expressions". For example, as illustrated in FIG. 7, the pre-conversion question "I don't want to be unable to have babies." has been converted into post-conversion questions such as "Could you please recommend a treatment method that ensures fertility?" and "Could you please tell me about pregnancy after the treatment, like oocyte cryopreservation?". Accordingly, the attending doctor is able to answer the questions of the patient, while including specific methods such as oocyte cryopreservation. Further, even with little medical knowledge, the patient is able to ask the attending doctor the questions while mentioning specific medical examples.

Alternatively, for example, the question converting function 502 may convert the questions by using an AI model (e.g., a DNN) configured to receive an input of a pre-conversion question and to output a post-conversion question represented by a "question using a more appropriate expression". In that situation, the AI model is generated by using training-purpose data in which pre-conversion questions represented by "questions using expressions that are not yet appropriate" serve as input data, whereas post-conversion questions represented by "questions using more appropriate expressions" serve as training data.

The post-conversion question transmitting function 503 is configured to output the second question. The post-conversion question transmitting function 503 is configured to transmit the post-conversion question generated by the question converting function 502 to the patient terminal 3 and to the attending doctor terminal 7 via the second communication I/F circuit 54 with predetermined timing. More specifically, the post-conversion question transmitting function 503 transmits the post-conversion question to the patient terminal 3 via the second communication I/F circuit 54. After that, when having received, from the patient terminal 3, an instruction to transmit the post-conversion question to the attending doctor terminal 7, the post-conversion question transmitting function 503 transmits the post-conversion question to the attending doctor terminal 7 via the second communication I/F circuit 54.

In this situation, the pre-conversion question obtaining function 501, the question converting function 502, and the post-conversion question transmitting function 503 are realized as a result of the second processing circuit 50 (i.e., the CPU) executing a controlling program. However, possible embodiments are not limited to this example, and it is also acceptable to realize a part or all of the pre-conversion question obtaining function 501, the question converting function 502, and the post-conversion question transmitting function 503 by using dedicated hardware designed to execute the same functions, such as a semiconductor integrated circuit (e.g., an ASIC, a DSP, or an FPGA), a conventional circuit module, or the like.

The second input I/F circuit 52 is connected to the second processing circuit 50 and is configured to convert input operations received from an operator into electrical signals and to output the electrical signals to the second processing circuit 50. For example, the second input I/F circuit 52 is realized by using a trackball, a switch button, a mouse, a keyboard, a touch panel, and/or the like.

The second display device 53 is connected to the second processing circuit 50 and is configured to display various types of information and various types of image data output from the second processing circuit 50. For example, the second display device 53 is realized by using a liquid crystal monitor, a CRT monitor, a touch panel, or the like.

The second communication I/F circuit 54 is connected to the second processing circuit 50 and is configured to control the transfer of various types of data and communication that are performed with the patient terminal 3, the attending doctor terminal 7, and the hospital database 9. For example, the second communication I/F circuit 54 is configured to receive the various types of data from the patient terminal 3 and the hospital database 9 and to output the received data to the second processing circuit 500. For example, the second communication I/F circuit 54 is realized by using a network card, a network adaptor, an NIC, or the like.

The Attending Doctor Terminal 7

For example, the attending doctor terminal 7 is an information processing apparatus (a computer) installed at a desk or the like of the attending doctor in the hospital. The attending doctor terminal 7 is configured to receive the post-conversion represented by the "question using a more appropriate expression" transmitted thereto from the question assisting server and to display the question in a predetermined format. Typically, the attending doctor terminal 7 is a personal computer (which may be of a tablet type).

Figure 8:
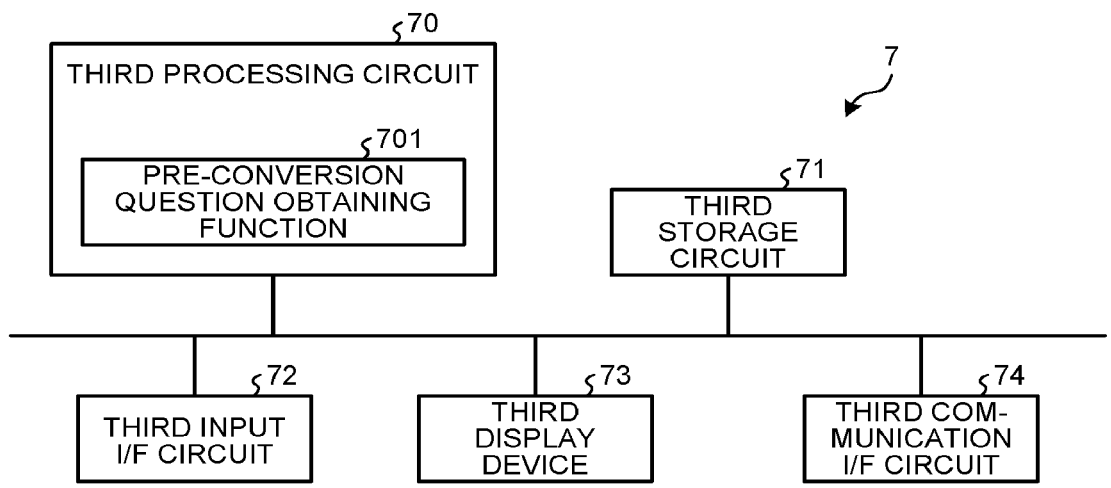
FIG. 8 is a diagram for explaining an exemplary configuration of an attending doctor terminal.

FIG. 8 is a diagram for explaining an exemplary configuration of the attending doctor terminal 7. As illustrated in FIG. 8, the attending doctor terminal 7 includes a third processing circuit 70, a third storage circuit 71, a third input I/F circuit 72, a third display device 73, and a third communication I/F circuit 74.

The third processing circuit 70 is a processor represented by a CPU configured to control the entire processes of the attending doctor terminal 7. For example, in response to an input operation received from an operator via the third input I/F circuit 72, the third processing circuit 70 is configured to control constituent elements of the attending doctor terminal 7. Further, for example, the third processing circuit 70 is configured to control the third display device 73 so as to display various types of data stored in the third storage circuit 71, a GUI used for performing various types of input processes, results of computing processes, and the like. Further, the third processing circuit 70 includes a pre-conversion question obtaining function 701.

The pre-conversion question obtaining function 701 is configured to obtain, via the third communication I/F circuit 74, the "question using a more appropriate expression" transmitted thereto from the question assisting server and to cause the third display device 73 to display the obtained question in a predetermine format.

In this situation, the pre-conversion question obtaining function 701 is realized as a result of the third processing circuit 70 (i.e., the CPU) executing a controlling program. However, possible embodiments are not limited to this example, and it is also acceptable to realize a part or all of the pre-conversion question obtaining function 701, by using dedicated hardware designed to execute the same functions, such as a semiconductor integrated circuit (e.g., an ASIC, a DSP, or an FPGA), a conventional circuit module, or the like.

The third storage circuit 71 is connected to the third processing circuit 70 and has stored therein a dedicated program or the like used for displaying questions (explained later). For example, the third storage circuit 71 is realized by using a semiconductor memory element such as a RAM or a flash memory, or a hard disk, an optical disk, or the like.

The third input I/F circuit 72 is connected to the third processing circuit 70 and is configured to convert input operations received from the operator into electrical signals and to output the electrical signals to the third processing circuit 70. For example, the third input I/F circuit 72 is realized by using a trackball, a switch button, a mouse, a keyboard, a touch panel, and/or the like.

The third display device 73 is connected to the third processing circuit 70 and is configured to display various types of information and various types of image data output from the third processing circuit 70. For example, the third display device 73 is realized by using a liquid crystal monitor, a CRT monitor, a touch panel, or the like.

The third communication I/F circuit 74 is connected to the third processing circuit 70 and is configured to control the transfer of various types of data and communication that are performed with the question assisting server and the hospital database 9. For example, the third communication I/F circuit 74 is configured to receive the various types of data from the question assisting server and the hospital database 9 and to output the received data to the third processing circuit 70. For example, the third communication I/F circuit 74 is realized by using a network card, a network adaptor, an NIC, or the like.

A Question Converting Process

Figure 9:
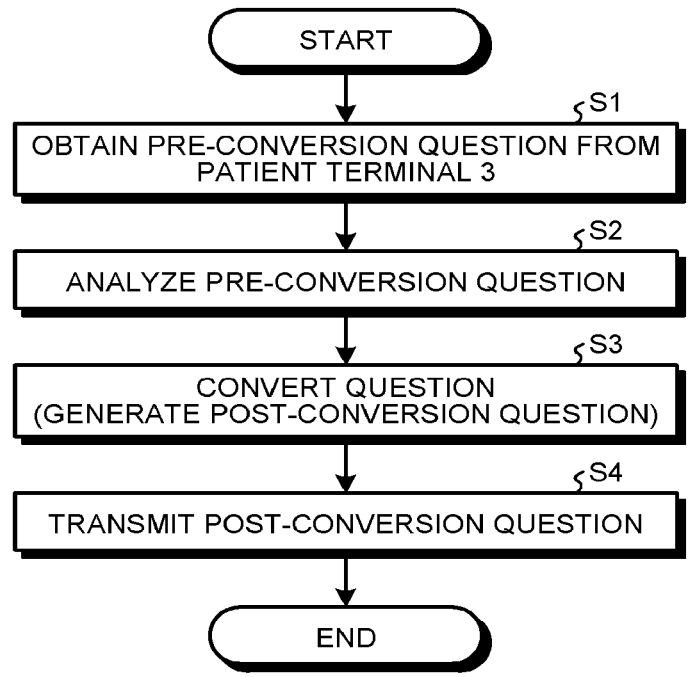
FIG. 9 is a flowchart illustrating an example of a flow in a question converting process performed by a question assisting server that serves as a diagnosis/treatment assisting apparatus according to the first embodiment.

FIG. 9 is a flowchart illustrating an example of a flow in a question converting process performed by the question assisting server 5 that serves as a diagnosis/treatment assisting apparatus α according to the first embodiment. The question converting process will be explained, with reference to FIG. 9.

As illustrated in FIG. 9, at first, the pre-conversion question obtaining function 501 obtains a pre-conversion question from the patient terminal 3 (step S1).

The question converting function 502 analyzes the pre-conversion question obtained from the patient terminal 3 (step S2). In other words, on the basis of the expressions contained in the obtained pre-conversion question, the question converting function 502 determines which of the pre-conversion questions registered in advance in the expression conversion table is applicable.

By referring to the expression conversion table, for example, the question converting function 502 generates a post-conversion question by converting the obtained pre-conversion question into a question using a more appropriate expression (step S3).

The post-conversion question transmitting function 503 transmits the post-conversion question generated by the question converting function 502 to the patient terminal 3 via the second communication I/F circuit 54 (step S4).

The post-conversion question obtaining function 304 of the patient terminal 3 obtains the post-conversion question from the question assisting server 5. The obtained post-conversion question is displayed on the first display device 33. The patient checks the content of the post-conversion question being displayed. Further, when two or more post-conversion questions are displayed, the patient selects one of the questions that is desirable.

If there is no discrepancy from the question which the patient wishes to ask, the patient instructs via the first input I/F circuit 32 that the question be transmitted to the doctor. The post-conversion question may be transmitted to the doctor from the patient terminal 3 or from the question assisting server 5 according to an instruction from the patient terminal 3.

The diagnosis/treatment assistance apparatus α according to the present embodiment described above includes: the pre-conversion question obtaining function 501 configured to obtain the pre-conversion question that is the first question represented by a question from the patient to the doctor; the question converting function 502 configured to analyze the content of the obtained pre-conversion question represented by the first question and, on the basis of the result of the analysis, to convert the pre-conversion question into the post-conversion question represented by the second question having the equivalent content and using the different expression; and the post-conversion question transmitting function 503 configured to output the post-conversion question. In other words, by converting the pre-conversion question created by the patient himself/herself, it is possible to generate the post-conversion question using the "medically appropriate expression" or the "expression that is polite and pays attention to subtleties". The generated post-conversion question is transmitted to the doctor after being checked by the patient himself/herself, for example.

Accordingly, in the situations where a doctor and a patient and his/her family need to communicate with each other such as when informed consent is carried out, it is possible to prevent the situation where the patient hesitates to ask a busy doctor questions about the doctor's experience and skills, medical risks, and the like having sensitive content to both parties and where the patient accepts a certain treatment method without being convinced. As a result, the doctor and the patient and his/her family are able to communicate with each other more smoothly. It is therefore possible to shorten the time required by the explanations, to be more efficient, and to improve the quality of the diagnosis/treatment process.

In view of informed consent as a background, advantageous effects achieved by the diagnosis/treatment assisting apparatus α according to the present embodiment will be explained further in detail. There are some problems that are unique to each patient and his/her family. For example, treatment for patients involves risks related to later complications and death, worries about being unable to pay the treatment expenses, financial problems such as having less or no income, having no relatives who can give care at the time of inpatient treatment, social problems where it may be difficult to return to society, and the like. Further, because of their busy schedules, it would be difficult for doctors to be involved with these problems unique to each patient and his/her family. It can be said that doctors do not address these problems unless patients or their families ask questions or ask for advice.

Further, patients and their families tend to hesitate to ask questions or ask for advice, because doctors are busy and because patients and their families are afraid that troubling doctors with questions or advice may cause disadvantages during the surgery or the postoperative care. Similarly, even when having an idea to get a second opinion, patients may not be able to request a second opinion, worrying that their relationship with their doctors may be adversely impacted afterwards. In those situations, patients and their families might blindly obey the doctors' explanations and proposals.

Further, in recent years, because there is abundance of medical information on the Internet, in particular, when patients and their families encounter information about a treatment method that is still at the study stage and is not completely proven scientifically or an alternative treatment method that is not well founded, the patients or their families may become suspicious that their doctors are intentionally hiding the information. There may be some situations where patients choose to quit a proper treatment at the hospital to undergo a treatment method that is not scientifically well founded, which will result in a disadvantage for the patients and their families.

By using the diagnosis/treatment assisting apparatus according to the present embodiment, it is possible to automatically convert the patient-oriented questions based on his/her own intentions into the expressions that are complemented with the medical information or the expressions that will not be impolite to the doctor. Consequently, in any of the abovementioned individual situations where informed consent is carried out or the like, the patient is able to ask the doctor the questions which he/she finds satisfactory. Further, the doctor is able to correctly understand what the patient really wants to know. As a result, the doctor and the patient and his/her family are able to communicate with each other more smoothly. It is therefore possible to shorten the time required by the explanations, to be more efficient, and to improve the quality of the diagnosis/treatment process.

First Modification Example

Next, a modification example of the question converting process performed by the question assisting server 5 serving as the diagnosis/treatment assisting apparatus α according to the first embodiment will be explained. In the present modification example, in the question converting process performed by the question assisting server 5, the question is further converted into individual questions, while taking into account attributes (question recipient attributes) of the doctor to whom the question is to be sent.

Figure 10:
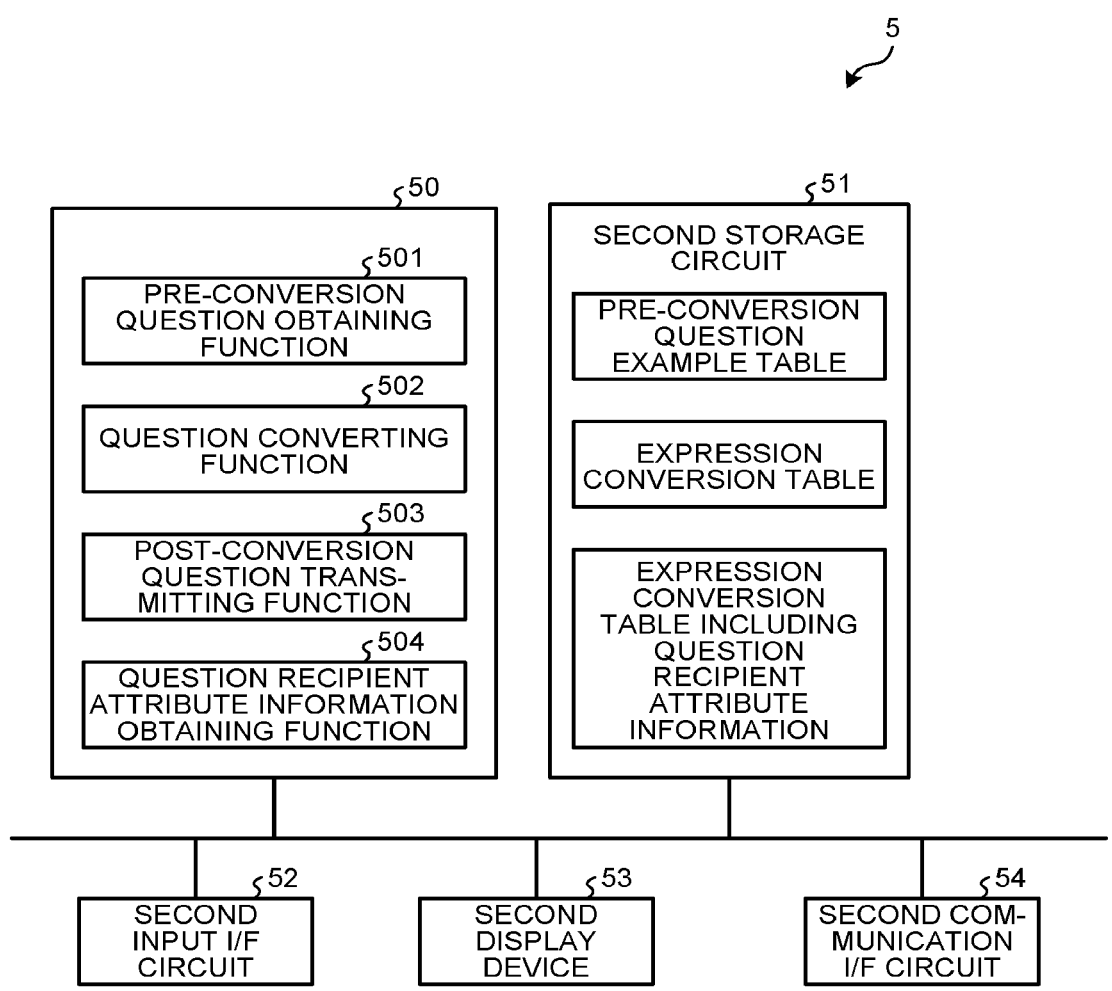
FIG. 10 is a diagram illustrating an exemplary configuration of a question assisting server according to a modification example.

FIG. 10 is a diagram illustrating an exemplary configuration of the question assisting server 5 according to the present modification example. As illustrated in FIG. 10, the question assisting server 5 according to the present modification example further includes a question recipient attribute information obtaining function 504, in addition to the configuration illustrated in FIG. 3. Further, the second storage circuit 51 has further stored therein an expression conversion table including the question recipient attributes.

In this situation, the expression conversion table including the question recipient attributes is a database in which the content of post-conversion questions is divided in subdivisions corresponding to doctors who are to receive the question, while taking into account attribute information (e.g., attributes such as the doctor's name, age, gender, whether or not he/she is a primary care doctor, the doctor's career, specialty, how many years he/she has worked at the hospital, whether he/she is a full-time or part-time doctor) of each of the doctors to whom the question is to be sent.

The question recipient attribute information obtaining function 504 is configured to obtain the attribute information (the question recipient attribute information) of the question recipient doctor from the patient terminal 3, the attending doctor terminal 7, the hospital database 9, and the like, via the Internet.

For example, the question converting function 502 is configured to convert a pre-conversion question transmitted from the patient terminal 3 into a post-conversion question represented by a question using a more appropriate expression, by using the attribute information obtained by the question recipient attribute information obtaining function 504 and the expression conversion table including the question recipient attributes (generating the post-conversion question).

FIG. 11 is a table illustrating examples indicating how pre-conversion questions have been converted into post-conversion questions, by using the attribute information and the expression conversion table including the question recipient attributes. For example, as illustrated in FIG. 11, let us discuss an example in which an elderly person who occasionally visits a hospital for swollen legs has created a pre-conversion question "I feel unsteady on my legs. Could you please provide a medication?". In this situation, when the question recipient is "the primary care doctor (Dr. A) who specializes in vascular surgery" according to the attribute information, because Dr. A knows the patient very well, a post-conversion question such as "The swelling worsened and made walking difficult. Please prescribe my regular medication." is generated. In another example, when the question recipient is "a part-time doctor on duty (Dr. B)" according to the attribute information, a post-conversion question such as "The swelling of my legs worsened and made walking difficult. Please prescribe Y mg X (a diuretic) as indicated in the chart." is generated, to describe the details of the usual treatment. In yet another example, when the question recipient is "a middle-ranked physician (Dr. C) who is not the primary care doctor" according to the attribute information, a post-conversion question such as "The swelling of my legs worsened and made walking difficult. Please prescribe the diuretic." is generated, to describe the cause while simplifying the details of the treatment. Supposedly, if Dr. C received the pre-conversion question "I feel unsteady on my legs. Could you please provide a medication?" without any conversion, there is a high possibility that the doctor would suspect that cerebral infarction might be the cause of feeling unsteady on his/her legs, which has a possibility of leading to unnecessary medical examinations and diagnosing process. In contrast, by appropriately converting the pre-conversion question while using the attribute information and the expression conversion table including the question recipient attributes, it is possible to prevent the situation where the unnecessary medical examinations and diagnosing process are required.

Further, for example, the question converting function 502 according to the modification example may also convert the question by using an AI model (a DNN) configured to receive an input of a pre-conversion question and to output a post-conversion question represented by a "question using a more appropriate expression while taking the question recipient attributes into account". In that situation, the AI model is generated by using training-purpose data in which pre-conversion questions represented by "questions using expressions that are not yet appropriate" serve as input data, whereas post-conversion questions represented by "questions using more appropriate expressions while question recipient attributes are taken into account" serve as training data.

In this situation, the question converting function 502 and the question recipient attribute information obtaining function 504 are realized as a result of the second processing circuit 50 (i.e., the CPU) executing a controlling program. However, possible embodiments are not limited to this example, and it is also acceptable to realize a part or all of the question converting function 502 and the question recipient attribute information obtaining function 504, by using dedicated hardware designed to execute the same functions, such as a semiconductor integrated circuit (e.g., an ASIC, a DSP, or an FPGA), a conventional circuit module, or the like.

FIG. 12 is a flowchart illustrating an example of a flow in the question converting process performed by the question assisting server 5 that serves as the diagnosis/treatment assisting apparatus α according to the first modification example. The question converting process will be explained, with reference to FIG. 12.

As illustrated in FIG. 12, at first, the pre-conversion question obtaining function 501 obtains a pre-conversion question from the patient terminal 3 (step S11).

The question recipient attribute information obtaining function 504 obtains the question recipient attribute information from the patient terminal 3, the attending doctor terminal 7, the hospital database 9, and/or the like, via the Internet (step S12).

The question converting function 502 analyzes the pre-conversion question obtained from the patient terminal 3 (step S13). In other words, on the basis of the expressions contained in the obtained pre-conversion question, the question converting function 502 determines which of the pre-conversion questions registered in advance in the expression conversion table is applicable.

By using the question recipient attribute information obtained at step S12 and the expression conversion table including the question recipient attributes, the question converting function 502 converts the pre-conversion question transmitted from the patient terminal 3 into a post-conversion question while taking the question recipient attribute information into account (generating the post-conversion question: step S14).

The post-conversion question transmitting function 503 transmits the post-conversion question generated at step S14 to the patient terminal 3 via the second communication I/F circuit 54 (step S15).

By using the question assisting server 5 serving as the diagnosis/treatment assisting apparatus α according to the first modification example described above, it is possible to generate the post-conversion question suitable for the purpose, while also taking into account the attributes of the doctor to whom the question is to be sent. As a result, in the situations where the doctor and the patient and his/her family need to communicate with each other, it is possible to make the communication smoother.

Second Modification Example

In the above embodiment, the example was explained in which the question assisting server 5, which is an independent apparatus, functions as the diagnosis/treatment assisting apparatus α. It is, however, not intended to limit possible embodiments to this example. For instance, the patient terminal 3 may function as the diagnosis/treatment assisting apparatus α.

Second Embodiment

Next, a diagnosis/treatment assisting system SY2 according to a second embodiment will be explained. The diagnosis/treatment assisting system SY2 according to the second embodiment is configured to predict and automatically generate a question which a patient and his/her family wish to ask a doctor about matters that may be found worrisome or questionable in the explanations given to the patient while informed consent is carried out or the like.

Figure 13:
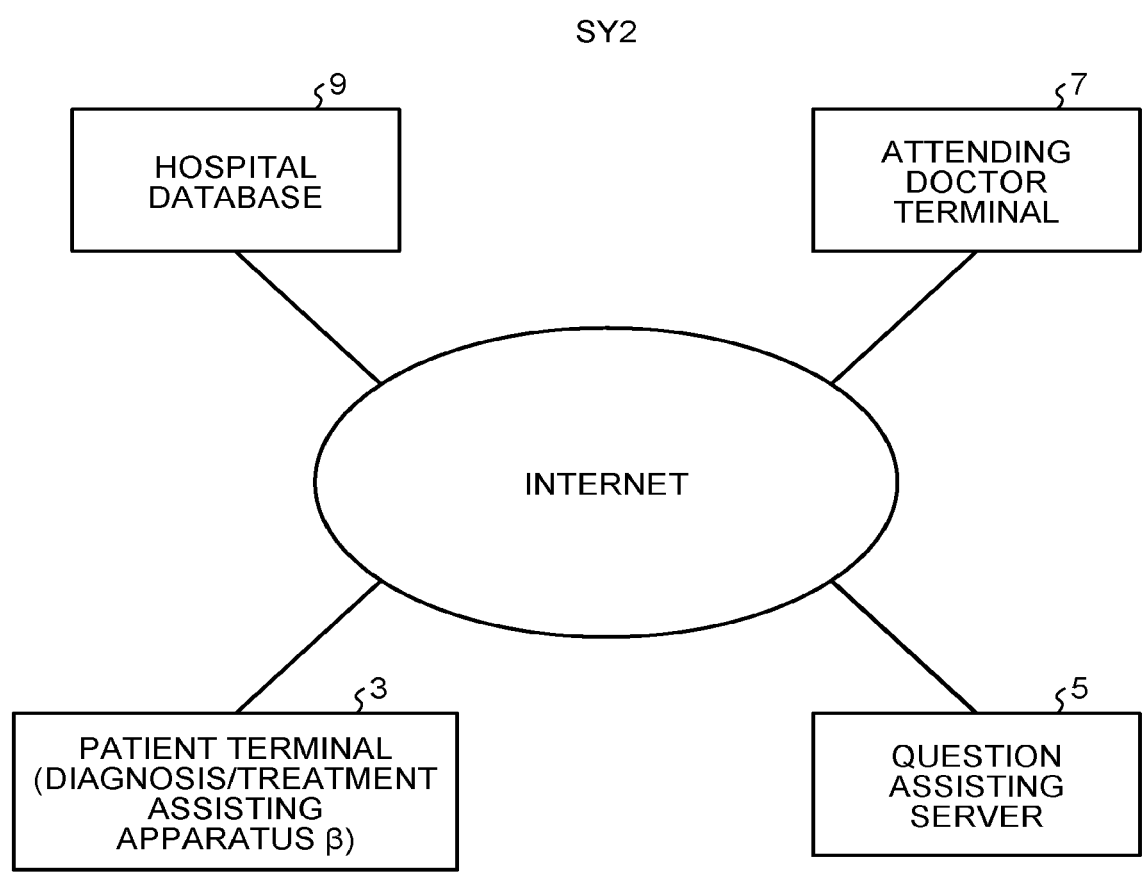
FIG. 13 is a diagram illustrating an exemplary configuration of a diagnosis/treatment assisting system according to a second embodiment.

FIG. 13 is a diagram illustrating an exemplary configuration of the diagnosis/treatment assisting system SY2 according to the second embodiment. As illustrated in FIG. 13, the diagnosis/treatment assisting system SY2 according to the present embodiment includes the patient terminal 3 serving as a diagnosis/treatment assisting apparatus β, the question assisting server, the attending doctor terminal 7, and the hospital database 9.

In FIG. 13, some of the constituent elements of the patient terminal 3, the question assisting server, the attending doctor terminal 7, and the hospital database 9 that are the same as those that have already been explained will be referred to by using the same reference characters, and detailed explanations thereof will be omitted.

The Patient Terminal 3

FIG. 14 is a diagram for explaining an exemplary configuration of the patient terminal 3 in the diagnosis/treatment assisting system SY2 according to the second embodiment. As illustrated in FIG. 14, the patient terminal 3 further includes a patient information obtaining function 305 and a patient information analyzing function 306, in addition to the configuration illustrated in FIG. 2. Further, the first storage circuit 31 has stored therein a characteristic description table (a characteristic description database) and a predicted question example table (a predicted question example database).

In the present example, the characteristic description table is a table in which descriptions of characteristics (characteristic descriptions) (explained later) are categorized in correspondence with combinations of various types of keywords included in obtained information and is a database searchable by using a keyword.

Further, the predicted question example table is a table in which questions generated in the past and anticipated questions generated in advance are categorized in correspondence with combinations of various types of keywords included in the characteristic descriptions. The predicted question example table is a database searchable by using any of the various types of keywords included in the characteristic descriptions.

The patient information obtaining function 305 is configured to obtain patient information.

In the present example, the patient information denotes information including at least one selected from among "information related to the patient", "medical information related to the patient", and "information related to activities of the patient".

The "information related to the patient" is information including at least one of the following: information related to the patient's family (whether the patient is married or not, his/her family structure, birthplace, etc.); information related to the patient's occupation (whether or not the patient is currently working, the current or past line of work; whether or not the patient is working as a medical provider; income, information related to the commute to work, etc.); information related to the patient's health (age, gender, height, weight, body fat, abdominal circumference, subcutaneous fat thickness, blood sugar, respiration, body movements, snoring noise, a current health condition, whether or not the patient has the habit of smoking, whether or not the patient has the habit of drinking alcohol, whether or not the patient has the habit of exercising; types of exercise, whether or not the patient has the habit of walking, the number of walking steps per day, average sleeping hours, life cycles in a day and a week, etc.); and information related to physical characteristics of the patient (blood pressure, heartrates, electrocardiograms, and blood oxygen saturation ($SpO_2$)).

The "medical information relate to the patient" is information such as diseases of the patient, treatment methods of the current diseases, the names of the medications being taken, previous medical history, and the like.

FIG. 15 is a table illustrating an example of medical information related to patients for each of the patients. As illustrated in FIG. 15, the medical information of each of the patients is indicated as: "Patient A: breast cancer, female, age 40; Has no previous major medical history. Her grandmother and mother have a history of breast cancer"; "Patient B: female, age 50, recurrent breast cancer; She had surgery, chemotherapy, and radiation therapy three years ago"; "Patient C: male, age 70; Diabetes has developed into diabetic nephropathy"; and "Patient D: female, age 40, breast cancer; Diagnosed as stage 2 and triple-negative type from test results; Imaging test results seem to exhibit no infiltration. Has no previous major medical history. Her grandmother and mother have a history of breast cancer. She has a health check-up every year". In this situation, it is possible to obtain the medical information related to the patients from the hospital database 9 or the like, for example, in a secure environment.

Further, the "information related to activities of the patient" is information including at least one selected from among: information about the patient on Social Networking Services (SNS); a purchase history of the patient using websites; a website browsing history of the patient; information about activities in the patient's daily life obtained from Information Technology [IT] device application software; and information related to electronic payments made by the patient (e.g., information related to credit card usage).

The details of the information related to the patient, the medical information related to the patient, and the information related to the activities of the patient described above are merely examples. Further, certain pieces of information may be duplicate among the information related to the patient, the medical information related to the patient, and the information related to the activities of the patient. For example, although the "age, gender, height, weight, body fat, abdominal circumference, subcutaneous fat thickness, blood sugar, and the like" are categorized as the information related to the patient in the above explanation, these items may also be obtained as the medical information related to the patient via the HIS or the like, for example. As another example, although "whether or not the patient has the habit of smoking, whether or not the patient has the habit of drinking alcohol, whether or not the patient has the habit of exercising; types of exercise, whether or not the patient has the habit of walking, the number of walking steps per day, average sleeping hours, life cycles in a day and a week, etc." are categorized as the information related to the patient in the above explanation, these items may also be obtained as the information related to activities of the patient via the patient terminal 3 or the like, for example.

The patient information obtaining function 305 is configured to obtain the patient information, via the patient terminal 3, other mobile phones and smartphones, wearable devices, and/or the like, or from information on the Internet such as SNS. Alternatively, the patient information obtaining function 305 may obtain the information through a direct input made by the patient via the first input I/F circuit 32.

The patient information analyzing function 306 corresponds to a second analyzing unit and is configured to determine at least one characteristic of the patient, by using at least the medical information related to the patient, the information related to the patient, and the information related to the activities of the patient. More specifically, by using at least the medical information related to the patient, the information related to the patient, and the information related to the activities of the patient, the patient information analyzing function 306 determines into at least which characteristics the patient can be categorized, among the eight characteristics listed below, for example.

(1) Innovative characteristics: characteristics related to accepting innovative medical care, e.g., which is preferable between innovative treatment methods and standard treatment methods.

(2) Risk characteristics: characteristics related to degrees of acceptance for complications and medical risks.

(3) Financial characteristics: characteristics related to financial situations, e.g., the capability to pay treatment expenses and whether the patient is willing to accept expensive medical care such as medical care not covered by insurances.

(4) Personality characteristics: characteristics related to the personality of the patient, e.g., whether the patient is optimistic, cautious, etc.
(5) Congeniality characteristics: characteristics related to being congenial to others, e.g., preferred types or personalities of doctors.
(6) Medical literacy characteristics: the amount of knowledge about medical care and the degree of understanding medical care.
(7) Health characteristics: characteristics related to health such as age, gender, habits of smoking, drinking alcohol, exercising, and sleeping, as well as physical characteristics.
(8) Family characteristics: characteristics related to the patient's family structure (whether the patient is married or not, the number of children (age/gender), living together or separately, etc.).

In some situations, one piece of information may correspond to more than one characteristic. For example, information related to innovative treatment methods may correspond to the innovative characteristics and the financial characteristics.

FIGS. 16 to 21 are tables illustrating examples of information which were obtained by the patient information obtaining function 305 and of which characteristics have been categorized by the patient information analyzing function 306.

More specifically, FIG. 16 is a table illustrating a result of analyzing characteristics, with regard to a purchase history of an individual (a patient) that serves as information related to activities of the patient. For example, as illustrated in FIG. 16, the "total purchase amount per month" is categorized as the "financial characteristics". The "purchase history of non-essential items and (online) lotteries" is categorized as the "personality characteristics", the "risk characteristics", and the "financial characteristics". The "purchase history of alcohol, cigarettes, etc." is categorized as the "financial characteristics", the "personality characteristics", the "risk characteristics", and the "innovative characteristics". Because the "purchase history of alcohol, cigarettes, etc." can also serve as information from a medical point of view, this piece of information is also categorized as "medical information".

Further, FIG. 17 is a table illustrating a result of analyzing characteristics, with regard to a web browsing history serving as information related to activities of the patient. For example, as illustrated in FIG. 17, the "web browsing history related to treatment methods in innovative medical care" is categorized as the "innovative characteristics" and the "medical literacy characteristics". Further, the "web browsing history related to treatment results" is categorized as the "risk characteristics", the "personality characteristics", and the "medical literacy characteristics". The "information preference (e.g., types of categories of news)" is categorized as the "personality characteristics", the "risk characteristics", the "innovative characteristics", the "medical literacy characteristics", and the "congeniality characteristics".

Further, FIG. 18 is a table illustrating a result of analyzing characteristics, with regard to tweet (post) information of the patient on SNS and the like that serves as information related to activities of the patient. For example, as illustrated in FIG. 18, the post "I'm going to have surgery soon. I'm very nervous." is categorized as the "personality characteristics" and the "medical literacy characteristics". Further, the post "I'm worried if I can pay the treatment expenses." is categorized as the "financial characteristics" and the "personality characteristics". The post "My doctor does not speak very candidly. I want to have a different doctor." is categorized as the "congeniality characteristics" and the "personality characteristics".

Further, FIG. 19 is a table illustrating a result of analyzing characteristics, with regard to information about activities in the patient's daily life that serves as information related to activities of the patient. For example, as illustrated in FIG. 19, activity information obtained from the patient terminal 3 such as "facilities visited by the patient, places to which the patient traveled, facilities used by the patient on a daily basis, and types of food the patient eats at restaurants" is categorized as the "financial characteristics", the "personality characteristics", the "innovative characteristics", and the "health characteristics".

Further, FIG. 20 is a table illustrating a result of categorizing characteristics, with regard to information related to the patient's family structure, occupation, income, and commute to work that serves as information related to activities of the patient. For example, in FIG. 20, the information obtained from an IT device such as "being married", and "having two children" is categorized as the "financial characteristics".

Further, FIG. 21 is a table illustrating a result of categorizing characteristics, with regard to information related to health, physical characteristics, and the like that serves as information related to activities of the patient. For example, in FIG. 21, "the number of walking steps" and "acceleration (an exercise amount per day: exercise intensity and duration)" obtained from the patient terminal 3 and/or a wearable device of the patient, for example, are categorized as the "personality characteristics". In this situation, because the information related to health, physical characteristics, and the like can also serve as information from a medical point of view, this type of information is also categorized as "medical information".

Returning to the description of FIG. 14, the patient information analyzing function 306 is configured to analyze the characteristics, by using the results of categorizing the information illustrated in FIGS. 16 to 21, for example. In this situation, analyzing the characteristics is a process of determining characteristics of the patient, on the basis of the various types of information aggregated for each of the characteristics.

In this situation, the patient information analyzing function 306 may be realized by using any means. For example, the patient information analyzing function 306 may be configured to extract frequently-used keywords from the information categorized in each of the characteristics of the patient and to further extract characteristic descriptions on the basis of the combination of the characteristic description database and the extracted keywords.

Further, the patient information analyzing function 306 may be realized by using an AI model (a DNN) configured to receive an input of a plurality of keywords for each characteristic and to output a description of the characteristic. In that situation, the AI model is generated by using training-purpose data in which a plurality of keywords for each characteristic serve as input data, whereas a characteristic description serves as training data.

FIG. 22 is a table for explaining examples of analysis results obtained by the patient information analyzing function 306. As illustrated in FIG. 22, the "innovative characteristics" of the patient are determined as "having a tendency to like/dislike standard medical care" and "having a tendency to like innovative medical care (e.g., whether the patient would like to receive treatment with a surgery robot or to have normal endoscopy surgery)".

FIG. 23 is a table for explaining other examples of analysis results (examples of another patient) obtained by the patient information analyzing function 306. As illustrated in FIG. 22, the "innovative characteristics" of the other patient are determined as follows: "The patient is a very career-oriented woman who was the first female to be promoted to manager in the company. She is full of motivation to be ahead of her time and has lots of curiosity."

Returning to the description of FIG. 14, the question generating function 302 is configured to generate a first question on the basis of the one or more characteristics resulting from the analysis. In other words, on the basis of the analysis results obtained by the patient information analyzing function 306, the question generating function 302 is configured to automatically generate the question which the patient and his/her family wish to ask the doctor about matters that may be found worrisome or questionable.

In this situation, the characteristic analyzing process performed by the patient information analyzing function 306 may be realized by using any means. For example, the patient information analyzing function 306 may extract frequently-used keywords from the information categorized in each of the characteristics of the patient. The patient information analyzing function 306 may further extract characteristic descriptions on the basis of the combination of the characteristic description database stored in the first storage circuit 31 and the extracted keywords. Further, the question may be converted by using an AI model (a DNN) configured to receive an input of a plurality of keywords for each characteristic and to output a description of the characteristic. In that situation, the AI model is generated by using training-purpose data in which a plurality of keywords for each characteristic serve as input data, whereas a characteristic description serves as training data.

FIG. 24 is a table for explaining examples of questions automatically generated by the question generating function 302. As illustrated in FIG. 24, on the basis of frequently-used keywords from the information categorized in each of the characteristics of the patient, for example, the following questions are automatically generated: "Why do I have breast cancer?", "Am I going to die?", and "I feel fulfilled with my work right now, and I don't want to start the treatment. (Would it possible to postpone the treatment?)".

FIG. 25 is a table for explaining other examples of questions automatically generated by the question generating function 302. As illustrated in FIG. 25, on the basis of frequency-used keywords from the information categorized in each of the characteristics of the patient, for example, a question such as "Please provide an easy-to-understand explanation of the side effects that may be experienced if the new drug is used." is automatically generated for a worry-wart patient with no medical knowledge. Further, for a patient who is taking an anticoagulant drug and prefers innovative treatments, a question such as "Why can't I have robot surgery right away?" is automatically generated.

The automatically-generated questions are based on the eight characteristics and the medical information of each patient. Accordingly, an appropriate question is predicted while taking personalities, orientation, financial circumstances, and the like of each patient into account.

The patient information obtaining function 305 and the patient information analyzing function 306 illustrated in FIG. 14 are realized as a result of the first processing circuit 30 (the CPU) executing a controlling program. However, possible embodiments are not limited to this example, and it is also acceptable to realize a part or all of the patient information obtaining function 305 and the patient information analyzing function 306, by using dedicated hardware designed to execute the same functions, such as a semiconductor integrated circuit (e.g., an ASIC, a DSP, or an FPGA), a conventional circuit module, or the like.

A Question Generating Process

Figure 26:
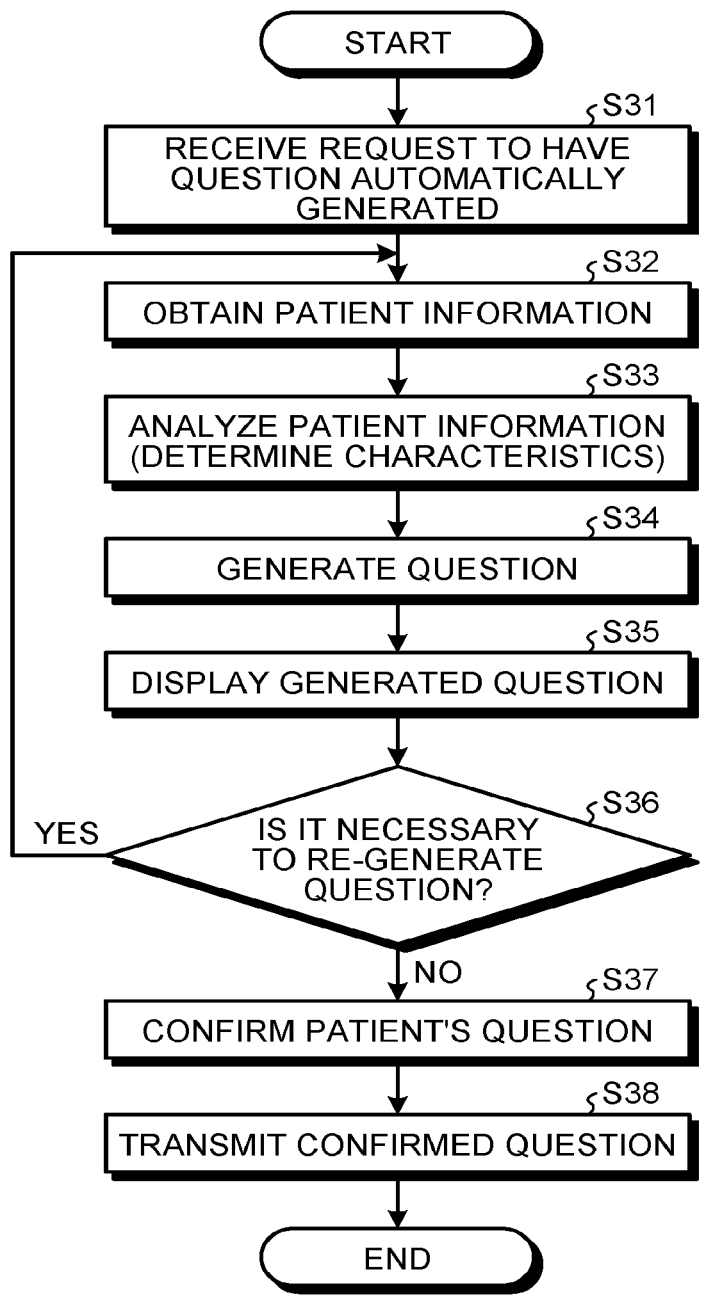
FIG. 26 is a flowchart illustrating an example of a flow in a question generating process.

FIG. 26 is a flowchart illustrating an example of a flow in a question generating process. The question generating process will be explained with reference to FIG. 26.

As illustrated in FIG. 26, at first, the question pre-conversion obtaining function 501 receives a request to have a question automatically generated from the patient terminal 3 (step S31).

The patient information obtaining function 305 obtains patient information from histories in the patient terminal, information on the Internet, and the like (step S32).

The patient information analyzing function 306 analyzes the patient information and determines at least one characteristic of the patient. More specifically, the patient information analyzing function 306 determines eight characteristics of the patient, by using at least the medical information related to the patient, the information related to the patient, and the information related to the activities of the patient (step S33).

On the basis of analysis results obtained by the patient information analyzing function 306, the question generating function 302 automatically generates a question (step S34). Further, the question generating function 302 causes the first display device 33 to display the generated question (step S35).

The patient checks the question displayed on the first display device 33. When the patient requests the question to be re-generated, a new condition is input through the first input I/F circuit to instruct the re-generating process (step S36: Yes). On the contrary, when the patient does not request the question to be re-generated, it is instructed to confirm the patient's question through the first input I/F circuit (step S36: No; and step S37). The confirmed question is transmitted to the question assisting server 5 and to the attending doctor terminal 7 each with certain timing (step S38).

The diagnosis/treatment assisting apparatus α according to the present embodiment described above includes: the patient information analyzing function 306 configured to determine at least one characteristic of the patient, by using at least the medical information related to the patient, the information related to the patient, and the information related to the activities of the patient; and the question generating function 302 configured to generate the first question represented by the question from the patient to the doctor on the basis of the determined one or more characteristics. The medical information related to the patient, the information related to the patient, and the information related to the activities of the patient may be obtained through a direct input made by the patient or may automatically be obtained from the information about the patient on SNS, the purchase history of the patient using websites, the website browsing history of the patient, the information about the activities in the patient's daily life obtained from application software in IT devices, the information related to electronic payments made by the patient (e.g., information related to credit card usage), and the like. The one or more characteristics of the patient are determined on the basis of these pieces of information that are automatically obtained. Also, the question from the patient to the doctor is automatically generated on the basis of the one or more characteristics of the patient.

Accordingly, for example, even in the situations where the patient or his/her family is unable to ask the doctor questions very well, is unable to think of a question, or is unable to say what he/she wants to say, when explanations are provided for the patient while informed consent is carried out, or the like, it is possible to automatically generate a question that takes into account versatile characteristics of each patient, without the need for particular work.

Further, because the question list is automatically generated about the matters which the patient and his/her family may find worrisome or questionable, it is possible to prevent the situation where the patient hesitates to ask questions of the doctor having a busy schedule and where the patient accepts a treatment method while not being convinced. As a result, the doctor and the patient and his/her family are able to communication with each other more smoothly. It is therefore possible to shorten the time required by the explanations, to be more efficient, and to improve the quality of the diagnosis/treatment process.

First Modification Example

In the above embodiment, the example was explained in which the patient information used for the categorization in the eight characteristics is primarily obtained automatically. In addition, it is also acceptable to obtain the patient information used for the categorization in the eight characteristics by, for example, asking the patient questions in an interactive format so as to have necessary information input. The following are examples of the questions corresponding to the characteristics listed for each of the characteristics.
(i) The innovative characteristics: "For the present case, do you want to search innovative treatment methods?"; "The following treatment methods were found in the search. Please select a treatment method in which you are interested.", or the like.
(ii) The risk characteristics: "Complications and medical risks that may occur are displayed for each treatment method. Please select treatment method(s) that you would (not) like to have. (or Please number them in the order of preference.)", or the like.
(iii) The financial characteristics: "Please enter your income.", "Please write down your family members.", "Do you have cancer insurance?", "The following is a list of expenses for each treatment method. Please select treatment method(s) that you would (not) like to have. (or Please number them in the order of preference.)", or the like.
(iv) The personality characteristics: "What type of personalities do you think you have? Write 'optimistic', 'cautious', or the like."; "Which would you prefer: a treatment method that statistically has a higher risk but has a higher possibility of a complete cure; or a step-by-step treatment method that takes time?", or the like.
(v) The congeniality characteristics: "What type of doctor would you like to have?"; "(For a female patient) Would you like to have a female doctor?", or the like.
(vi) The medical literacy characteristics: "Have you researched about breast cancer?"; "In what type of folk remedies are you interested?", or the like.
(vii) The health characteristics: "Do you have the habit of smoking?", "Do you have the habit of drinking alcohol?", or the like.
(viii) The family characteristics: "Are you married?", "How many people are there in your family?", "If you need to be hospitalized, is there anyone who can take care of you?", or the like.

Second Modification Example

In the above embodiment, the example was explained in which the first storage circuit 31 has stored therein the characteristic description table and the predicted question example table. However, the characteristic description table and the predicted question example table do not necessarily have to be stored in the patient terminal 3. For example, another arrangement is also acceptable in which the characteristic description table and the predicted question example table are stored in the second storage circuit 51 of the question assisting server 5, so as to be accessed via the Internet when necessary.

Third Embodiment

Next, a diagnosis/treatment assisting system SY3 according to a third embodiment will be explained. The diagnosis/treatment assisting system SY3 according to the second embodiment is obtained by combining the diagnosis/treatment assisting system SY1 according to the first embodiment with the diagnosis/treatment assisting system SY2 according to the second embodiment.

FIG. 27 is a diagram illustrating an exemplary configuration of the diagnosis/treatment assisting system SY3 according to the third embodiment. As illustrated in FIG. 27, the diagnosis/treatment assisting system SY1 according to the present embodiment includes the patient terminal 3 serving as the diagnosis/treatment assisting apparatus β, the question assisting server 5 serving as the diagnosis/treatment assisting apparatus α, the attending doctor terminal 7, and the hospital database 9.

In other words, by transmitting, to the question assisting server 5, a question automatically generated by the patient terminal 3 as a pre-conversion question, it is possible to convert the automatically-generated question into a question using a more appropriate expression.

Consequently, by using the diagnosis/treatment assisting system SY3 according to the present embodiment, it is possible to communicate the question based on the versatile characteristics of each patient to the doctor, by using a medically appropriate expression or an expression that is polite and pay attention to subtleties. As a result, the doctor and the patient and his/her family are able to communicate with each other more smoothly. It is therefore possible to shorten the time required by the explanations, to be more efficient, and to improve the quality of the diagnosis/treatment process.

The term "processor" used in the above explanations denotes, for example, a CPU, a Graphics Processing Unit (GPU), or circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing programs saved in a storage circuit. Alternatively, instead of saving the programs in the storage circuit, it is also acceptable to directly incorporate the programs into the circuits of the processors. In that situation, the processors realize the functions by reading and executing the programs incorporated in the circuits thereof. Further, the processors of the present embodiments do not each necessarily have to be configured as a single circuit. It is also acceptable to structure one processor by combining together two or more independent circuits so as to realize the functions thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A diagnosis/treatment assisting apparatus, comprising: processing circuitry configured to
    obtain a first question to a doctor, the first question being related to medical treatment of a patient and being entered by the patient via a graphical user interface (GUI) displayed on a terminal of the patient,
    automatically without human intervention, generate at least one question candidate by inputting at least one keyword extracted from the first question entered via the GUI into a first machine-learning model, which outputs the at least one question candidate, wherein the first machine-learning model is trained using a first training set including input keywords and corresponding questions serving as first training data,
    automatically without human intervention, convert the generated at least one question candidate output by the first machine-learning model into a second question by inputting the generated at least one question candidate into a second machine-learning model, which outputs the second question, the second question having equivalent content, but using a different expression, wherein the second machine-learning model is trained using a second training set including inappropriate questions as input data and corresponding appropriate questions as second training data;
    transmit the second question output by the second machine-learning model over a network to the terminal of the patient for display on the terminal of the patient, and
    transmit the second question output by the second machine-learning model over the network to a terminal of the medical doctor in response to an instruction received from the terminal of the patient, the instruction being received based on input by the patient to the user interface, after the second question is displayed on the terminal of the patient and approved by the patient, so that the patient receives an answer related to the medical treatment of the patient prior to performance of the medical treatment of the patient.

2. The diagnosis/treatment assisting apparatus according to claim 1, wherein the processing circuitry is further configured to change the obtained first question into the second question corrected with a medical expression.

3. The diagnosis/treatment assisting apparatus according to claim 1, wherein the processing circuitry is further configured to change the obtained first question into the second question corrected with an expression paying attention to subtleties.

4. The diagnosis/treatment assisting apparatus according to claim 1, wherein the processing circuitry is further configured to change the obtained first question into the second question in accordance with attribute information of the medical doctor.

5. The diagnosis/treatment assisting apparatus according to claim 1, wherein the processing circuitry is further configured to determine at least one characteristic of the patient, by using at least medical information related to the patient, information related to the patient, and information related to an activity of the patient, and generate the first question based on said at least one characteristic having been analyzed.

6. The diagnosis/treatment assisting apparatus according to claim 5, wherein the processing circuitry is further configured to determine said at least one characteristic of the patient by using at least one of the following as the information related to the activity of the patient: information about the patient on a Social Networking Service (SNS), a purchase history of the patient using a website, a website browsing history of the patient, activity information of the patient obtained from an Information Technology (IT) device, and information related to an electronic payment made by the patient.

7. The diagnosis/treatment assisting apparatus according to claim 5, wherein the processing circuitry is further configured to determine said at least one characteristic of the patient by using at least one of the following as the information related to the patient: information related to family of the patient, information related to an occupation of the patient, information related to health of the patient, and information related to a physical characteristic of the patient.

8. The diagnosis/treatment assisting apparatus according to claim 5, wherein, as said at least one characteristic of the patient, the processing circuitry is further configured to analyze at least one of the following: an innovative characteristic that is a characteristic related to the patient accepting innovative medical care, a risk characteristic that is a characteristic related to the patient accepting a medical risk, a financial characteristic that is a characteristic related to a financial situation of the patient; a personality characteristic that is a characteristic related to a personality of the patient, a congeniality characteristic related to congeniality of the patient with the medical doctor, a medical literacy characteristic that is a characteristic related to medical literacy of the patient, a health characteristic that is a characteristic related to health of the patient, and a family characteristic that is a characteristic related to a family structure of the patient.

9. The diagnosis/treatment assisting apparatus of claim 1, wherein the processing circuitry is configured to convert the at least one question candidate into the second question, which is in a same language as the first question.

10. The diagnosis/treatment assisting apparatus of claim 1, wherein the processing circuitry is further configured to
    create the first training set including the input keywords and the corresponding questions serving as the first training data, and train the first machine-learning model, using a first training process, to output a question based on keyword inputs, using the first training set, and
    create the second training set including the inappropriate questions as the input data and the corresponding appropriate questions as the second training data, and train the second machine-learning model, using a second training process, to output an appropriate question based on an input inappropriate question, using the second training set.

11. A diagnosis/treatment assisting apparatus, comprising: processing circuitry to
- determine at least one characteristic of a patient, by using at least medical information related to the patient, information related to the patient, and information related to an activity of the patient,
- automatically without human intervention, generate a first question, related to medical treatment of the patient, from the patient to a medical doctor based on said at least one characteristic,
- automatically without human intervention, generate at least one question candidate by inputting at least one keyword extracted from the generated first question into a first machine-learning model, which outputs the at least one question candidate, wherein the first machine-learning model is trained using a first training set including input keywords and corresponding questions serving as first training data,
- automatically without human intervention, convert the generated at least one question candidate output by the first machine-learning model into a second question by inputting the generated at least one question candidate into a second machine-learning model, which outputs the second question, the second question having equivalent content, but using a different expression, wherein the second machine-learning model is trained using a second training set including inappropriate questions as input data and corresponding appropriate questions as second training data,
- transmit the second question output by the second machine-learning model over a network to a terminal of the patient for display on the terminal of the patient, and
- transmit the second question output by the second machine-learning model over the network to a terminal of the medical doctor, in response to an instruction received from the terminal of the patient, the instruction being received based on input by the patient to a user interface, after the second question is displayed on the terminal of the patient and approved by the patient, so that the patient receives an answer related to the medical treatment of the patient prior to performance of the medical treatment of the patient.

12. A diagnosis/treatment assisting system, comprising:
a first processing circuit configured to
- determine at least one characteristic of a patient by using at least medical information related to the patient, information related to the patient, and information related to an activity of the patient, and
- automatically without human intervention, generate a first question, related to medical treatment of the patient, from the patient to a medical doctor based on said at least one characteristic, and a second processing circuit configured to
- automatically without human intervention, generate at least one question candidate by inputting at least one keyword extracted from the first question into a first machine-learning model, which outputs the at least one question candidate, wherein the first machine-learning model is trained using a first training set including input keywords and corresponding questions serving as first training data,
- automatically without human intervention, convert the generated at least one question candidate output by the first machine-learning model into a second question by inputting the generated at least one question candidate into a second machine-learning model, which outputs the second question, the second question having equivalent content, but using a different expression, wherein the second machine-learning model is trained using a second training set including inappropriate questions as input data and corresponding appropriate questions as second training data,
- transmit the second question output by the second machine-learning model over a network to a terminal of the patient for display on the terminal of the patient, and
- transmit the second question output by the second machine-learning model over the network to a terminal of the medical doctor in response to an instruction received from the terminal of the patient, the instruction being received based on input by the patient to a user interface, after the second question is displayed on the terminal of the patient and approved by the patient, so that the patient receives an answer related to the medical treatment of the patient prior to performance of the medical treatment of the patient.

13. The diagnosis/treatment assisting system according to claim 12, wherein the second processing circuit is further configured to change the obtained first question into the second question corrected with a medical expression.

14. The diagnosis/treatment assisting system according to claim 12, wherein the second processing circuit is further configured to change the obtained first question into the second question corrected with an expression paying attention to subtleties.

15. The diagnosis/treatment assisting system according to claim 12, wherein the second processing circuit is further configured to change the obtained first question into the second question in accordance with attribute information of the medical doctor.

16. The diagnosis/treatment assisting system according to claim 12, wherein the first processing circuit is further configured to determine said at least one characteristic of the patient by using at least one of the following as the information related to the activity of the patient: information about the patient on a Social Networking Service (SNS), a purchase history of the patient using a website, a website browsing history of the patient, activity information of the patient obtained from an Information Technology (IT) device, and information related to an electronic payment made by the patient.

17. The diagnosis/treatment assisting system according to claim 12, wherein the first processing circuit is further configured to determine said at least one characteristic of the patient by using at least one of the following as the information related to the patient: information related to family of the patient, information related to an occupation of the patient, information related to health of the patient, and information related to a physical characteristic of the patient.

18. The diagnosis/treatment assisting system according to claim 12, wherein, as said at least one characteristic of the patient, the first processing circuit is further configured to analyze at least one of the following: an innovative characteristic that is a characteristic related to the patient accepting innovative medical care, a risk characteristic that is a characteristic related to the patient accepting a medical risk, a financial characteristic that is a characteristic related to a financial situation of the patient, a personality characteristic that is a characteristic related to a personality of the patient, a congeniality characteristic related to congeniality of the patient with the medical doctor, a medical literacy characteristic that is a characteristic related to medical literacy of the patient, a health characteristic that is a characteristic related to health of the patient, and a family characteristic that is a characteristic related to a family structure of the patient.

* * * * *